(12) United States Patent
Usas et al.

(10) Patent No.: US 9,199,003 B2
(45) Date of Patent: Dec. 1, 2015

(54) BONE AUGMENTATION UTILIZING MUSCLE-DERIVED PROGENITOR COMPOSITIONS IN BIOCOMPATIBLE MATRIX, AND TREATMENTS THEREOF

(75) Inventors: Arvydas Usas, Pittsburgh, PA (US);
Karin Payne, Pittsburgh, PA (US);
Thomas Payne, Pittsburgh, PA (US);
Ronald Jankowski, Pittsburgh, PA (US);
Johnny Huard, Waxford, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 520 days.

(21) Appl. No.: 12/543,311

(22) Filed: Aug. 18, 2009

(65) Prior Publication Data

US 2010/0215623 A1    Aug. 26, 2010

Related U.S. Application Data

(60) Provisional application No. 61/089,798, filed on Aug. 18, 2008, provisional application No. 61/166,775, filed on Apr. 6, 2009.

(51) Int. Cl.

| | | |
|---|---|---|
| *A61L 27/38* | (2006.01) | |
| *A61K 35/38* | (2015.01) | |
| *C12N 5/077* | (2010.01) | |
| *A61L 27/36* | (2006.01) | |
| *A61L 27/54* | (2006.01) | |
| *A61L 27/58* | (2006.01) | |
| *C12N 11/02* | (2006.01) | |
| *A61K 35/12* | (2015.01) | |

(52) U.S. Cl.
CPC ............ *A61L 27/3895* (2013.01); *A61K 35/38* (2013.01); *A61L 27/365* (2013.01); *A61L 27/3629* (2013.01); *A61L 27/3847* (2013.01); *A61L 27/54* (2013.01); *A61L 27/58* (2013.01); *C12N 5/0659* (2013.01); *C12N 11/02* (2013.01); *A61K 35/12* (2013.01); *A61L 2300/64* (2013.01); *A61L 2430/02* (2013.01); *A61L 2430/40* (2013.01); *C12N 2533/92* (2013.01)

(58) Field of Classification Search
CPC ... A61K 35/38; C12N 5/0659; A61L 27/3629
See application file for complete search history.

(56) References Cited

U.S. PATENT DOCUMENTS

| | | |
|---|---|---|
| 4,424,208 A | 1/1984 | Wallace et al. |
| 4,965,353 A | 10/1990 | Della Valle et al. |
| 5,045,601 A | 9/1991 | Capelli et al. |
| 5,053,050 A | 10/1991 | Itay |
| 5,130,141 A | 7/1992 | Law et al. |
| 5,206,028 A | 4/1993 | Li |
| 5,336,263 A | 8/1994 | Ersek et al. |
| 5,443,950 A | 8/1995 | Naughton et al. |
| 5,510,254 A | 4/1996 | Naughton et al. |
| 5,516,532 A | 5/1996 | Atala et al. |
| 5,538,722 A | 7/1996 | Blau et al. |
| 5,541,107 A | 7/1996 | Naughton et al. |
| 5,594,032 A | 1/1997 | Gonzalez-Cadavid et al. |
| 5,656,478 A | 8/1997 | Tanagho et al. |
| 5,667,778 A | 9/1997 | Atala |
| 5,733,337 A | 3/1998 | Carr, Jr. et al. |
| 5,785,964 A | 7/1998 | Naughton et al. |
| 5,833,978 A | 11/1998 | Tremblay |
| 5,842,477 A | 12/1998 | Naughton et al. |
| 5,858,351 A | 1/1999 | Podsakoff et al. |
| 5,858,390 A | 1/1999 | Boss |
| 5,858,721 A | 1/1999 | Naughton et al. |
| 5,863,531 A | 1/1999 | Naughton et al. |
| 5,876,447 A | 3/1999 | Arnett |
| 5,902,741 A | 5/1999 | Purchio et al. |
| 5,962,325 A | 10/1999 | Naughton et al. |

(Continued)

FOREIGN PATENT DOCUMENTS

| | | |
|---|---|---|
| AU | 2006202380 A1 | 6/2007 |
| CA | 2438904 A1 | 9/2002 |

(Continued)

OTHER PUBLICATIONS

Voytik-Harbin & Badylak, "Induction of Osteogenic Activity by Small Intestinal Submucosa in Rat Calvaria Non-union Defects", First SIS Symposium, Dec. 1996, p. 1.*

Keskin et al., "Repairing Critical-Sized Rat Calvarial Defects With a Periosteal Cell-Seeded Small Intestinal Submucosa Layer", Plastic and Reconstructive Surgery, Aug. 2008, vol. 122, No. 2, pp. 400-409.*

Acsadi et al., (1994). "A differential efficiency of adenovirus-mediated in vivo gene transfer into skeletal muscle cells of different maturity", Hum. Mol. Genetics, 3(4):579-584.

(Continued)

*Primary Examiner* — Laura Schuberg
(74) *Attorney, Agent, or Firm* — Mintz Levin Cohn Ferris Glovsky and Popeo, P.C.; Shovon Ashraf

(57) ABSTRACT

The present invention provides muscle-derived progenitor cells that show long-term survival following transplantation into body tissues and which can augment non-soft tissue following introduction (e.g. via injection, transplantation, or implantation) into a site of non-soft tissue (e.g. bone) when combined with a biocompatible matrix, preferably SIS. The invention further provides methods of using compositions comprising muscle-derived progenitor cells with a biocompatible matrix for the augmentation and bulking of mammalian, including human, bone tissues in the treatment of various functional conditions, including osteoporosis, Paget's Disease, osteogenesis imperfecta, bone fracture, osteomalacia, decrease in bone trabecular strength, decrease in bone cortical strength and decrease in bone density with old age.

7 Claims, 6 Drawing Sheets
(6 of 6 Drawing Sheet(s) Filed in Color)

(56) References Cited

U.S. PATENT DOCUMENTS

| | | | |
|---|---|---|---|
| 6,001,654 | A | 12/1999 | Anderson et al. |
| 6,099,832 | A | 8/2000 | Mickle et al. |
| 6,121,042 | A | 9/2000 | Peterson et al. |
| 6,171,340 | B1 | 1/2001 | McDowell |
| 6,174,333 | B1 | 1/2001 | Kadiyala et al. |
| 6,261,832 | B1 | 7/2001 | Law |
| 6,299,905 | B1 | 10/2001 | Peterson et al. |
| 6,348,069 | B1 | 2/2002 | Vacanti et al. |
| 6,482,645 | B2 | 11/2002 | Atala |
| 6,503,504 | B1 | 1/2003 | Vandenburgh |
| 6,866,842 | B1 | 3/2005 | Chancellor et al. |
| 6,986,735 | B2 | 1/2006 | Abraham et al. |
| 7,115,417 | B1 | 10/2006 | Chancellor et al. |
| 7,141,072 | B2 | 11/2006 | Geistlich et al. |
| 7,147,846 | B2 | 12/2006 | Anderson et al. |
| 7,427,284 | B2 | 9/2008 | Seedhom et al. |
| 7,887,792 | B2 | 2/2011 | Chancellor et al. |
| 7,906,110 | B2 | 3/2011 | Chancellor et al. |
| 2002/0090389 | A1 | 7/2002 | Humes et al. |
| 2005/0048039 | A1 | 3/2005 | Dreyfus et al. |
| 2005/0220775 | A1* | 10/2005 | Chancellor et al. ........ 424/93.21 |
| 2005/0238625 | A1 | 10/2005 | Chancellor et al. |
| 2005/0265978 | A1 | 12/2005 | Chancellor et al. |
| 2006/0078993 | A1* | 4/2006 | Phan et al. .................... 435/366 |
| 2006/0280726 | A1 | 12/2006 | Chancellor et al. |
| 2007/0065416 | A1 | 3/2007 | Chancellor et al. |
| 2007/0065417 | A1 | 3/2007 | Chancellor et al. |
| 2008/0152627 | A1* | 6/2008 | Chancellor et al. .......... 424/93.7 |

FOREIGN PATENT DOCUMENTS

| | | | |
|---|---|---|---|
| JP | 2007275613 A | 10/2007 | |
| WO | WO 91/07992 | 6/1991 | |
| WO | WO 94/07999 | 4/1994 | |
| WO | WO 94/21299 | 9/1994 | |
| WO | WO-9425080 A1 | 11/1994 | |
| WO | WO 96/18303 | 6/1996 | |
| WO | WO 98/36055 | 8/1998 | |
| WO | WO 98/44142 | 10/1998 | |
| WO | WO 98/54301 | 12/1998 | |
| WO | WO 99/47163 | 9/1999 | |
| WO | WO-9946366 A1 | 9/1999 | |
| WO | WO 99/56785 | * 11/1999 | ............ A61K 48/00 |
| WO | WO 99/56786 | 11/1999 | |
| WO | WO 00/17322 | 3/2000 | |
| WO | WO 00/29552 | 5/2000 | |
| WO | WO 01/19966 | 3/2001 | |
| WO | WO 01/78754 | 10/2001 | |
| WO | WO 02/067887 | 9/2002 | |
| WO | WO 2007/024441 | * 3/2007 | ............... C12N 5/08 |
| WO | WO-2008076435 A1 | 6/2008 | |
| WO | WO 2009/045506 | 4/2009 | |

OTHER PUBLICATIONS

Alden et al., (1999). "In Vivo Endochondral Bone Formation Using a Bone Morphogenetic Protein 2 Adenoviral Vector", Hum. Gene Ther., 10:2245-2253.

Anderson (1998). "Human gene therapy", Nature, 392:25-30.

Andrews et al., (1986). "Monoclonal Antibody 12-8 Recognizes a 115-kd Molecule Present on Both Unipotent and Multipotent Hematopoietic Colony-Forming Cells and Their Precursors", Blood, 67:842-845.

Anwer et al., (1998). "Systemic Effect of Human Growth Hormone After Intramuscular Injection of a Single Dose of a Muscle-Specific Gene Medicine", Hum. Gene Ther., 9:659-670.

Arcila et al., (1997). "Mass and Functional Capacity of Regenerating Muscle Is Enhanced by Myoblast Transfer", J. Neurobiol., 33:185-198.

Ashman et al., (1999). "", Int. J. Biochem. Cell. Biol. 31:1037-1051.

Atkins et al., (1999). "Intracardiac Transplantation of Skeletal Myoblasts Yields Two Populations of Striated Cells In Situ", Ann. Thorac. Surg., 67:124-129.

Atkins et al., (1999). "Myogenic Cell Transplantation Improves In Vivo Regional Performance in Infarcted Rabbit Myocardium", J. Heart Lung Transplant., 18:1173-1180.

Bandara et al., (1993). "Intraarticular expression of biologically active interleukin 1-receptor-antagonist protein by ex vivo gene transfer", Proc. Natl. Acad. Sci., 90:10764-10768.

Baroffio et al., (1996). "Identification of self-renewing myoblasts in the progeny of single human muscle satellite cells", Differentiation, 60:47-57.

Barr & Leiden (1991). "Systemic Delivery of Recombinant Proteins by Genetically Modified Myoblasts", Science, 254:1507-1509.

Beauchamp et al., (1999). "Dynamics of Myoblast Transplantation Reveal a Discrete Minority of Precursors with Stem Cell-like Properties as the Myogenic Source", J. Cell Biol., 144:1113-1122.

Blanton et al. (1999). "Isolation of two populations of myoblasts from porcine skeletal muscle", Muscle Nerve, 22:43-50.

Cannon et al., (2003). "Improved sphincter contractility after allogenic muslce-derived progenitor cell injection into the denervated rat urethra", Urology, 62(5):958-963.

Chancellor et al., (2000), "Preliminary Results of Myoblast Injection into the Urethra and Bladder Wall: A Possible Method for the Treatment of Stress Urinary Incontinence and Impaired Detrusor Contractility", Neurourology and Urodynamics, 19(3):279-287.

Chancellor et al., (2001). "Gene therapy strategies for urological dysfunction", Trends Mol. Med., 7(7):301-306.

Civin et al., (1984). "Antigenic Analysis of Hematopoiesis: A Hematopoietic Progenitor Cell Surface Antigen Defined by a Monoclonal Antibody Raised against KG-la Cells", J. Immunol. 133:157-165.

Dalle et al., (1999). "Improvement of mouse beta-thalassemia upon erythropoietin delivery by encapsulated myoblasts", Gene Ther., 6:157-161.

Dana et al., (1998). "Interleukin-1 Receptor Antagonist Suppresses Langerhans Cell Activity and Promotes Ocular Immune Privilege", Investigative Ophthalmology & Visual Science, 39:70-77.

Database accession No. EMB-1995233867, (1995), "Genuine stress urinary incontinence with low urethral pressure: Five-year follow-up after the Ball-Burch procedure", Journal of Reproductive Medicine for the Obstetrician and Gynecologist, 40(7):503-506.

Day et al., (1997). "Myoblast-Mediated Gene Transfer to the Joint", J. of Orthopedic Research, 15:894-903.

Deasy et al., (2002). "Gene therapy and tissue engineering based on muscle-derived stem cells", Current Opinion in Molecular Therapeutics, 4:382-389.

Dhawan et al., (1992). "Systemic Delivery of Human Growth Hormone by Injection of Genetically Engineered Myoblasts", Science, 254:1509-1512.

Dominov et al., (1998). "Bcl-2 Expression Identifies an Early Stage of Myogenesis and Promotes Clonal Expansion of Muscle Cells", J. Cell Biol., 142:537-544.

European Search Report, Application No. EP08169379.8, Date: Mar. 9, 2009.

European Supplementary Search Report, Appl. No. EP 02706457, Mailed on May 27, 2009.

Faustman et al., (1991). "Prevention of Xenograft Rejection by Masking Donor HLA Class I Antigens", Science, 252:1701.

Ferrari et al., (1998). "Muscle Regeneration by Bone Marrow-Derived Myogenic Progenitors", Science, 279:1528-1530.

Fina et al., (1990). "Expression of the CD34 Gene in Vascular Endothelial Cells", Blood, 75:2417-2426.

Friedmann (2000). "Principles for Human Gene Therapy Studies", Science, 287(5461):2163-2165.

Fukuda et al., (2000), "Regenerative Medicine and Life Science—Reproductive Engineering, Stem cell Engineering, and Tissue Engineering", Tanpakushita Kakusan Kouso (Protein, Nucleic Acid and Enzyme) 45(13), 2078-2084. (Abstract only in English).

Garban et al., (1997). "Cloning of Rat and Human Inducible Penile Nitric Oxide Synthase. Application for Gene Therapy of Erectile Dysfunction", Biol. Reprod., 56(4):954-963.

Grinnell A. D., (1994). "Trophic Interaction Between Nerve and Muscle", Myology Ed. 2, A. G. Engel & C. F. Armstrong, McGraw-Hill, Inc., 303-304.

Gros et al., (1999). "Insulin Production by Engineered Muscle Cells", Hum. Gene Ther., 10:1207-1217.

(56) References Cited

OTHER PUBLICATIONS

Gross et al., (1999). "Muscle Precursor Cells Injected into Irradiated mdx Mouse Muscle Persistent After Serial Injury", Muscle & Nerve, 22:174-185.
Gussoni et al., (1992). "Normal dystrophin transcripts detected in Duchenne muscular dystrophy patients after myoblast transplantation", Nature, 356:435-438.
Gussoni et al., (1999). "Dystrophin expression in the mdx mouse restored by stem cell transplantation", Nature, 401:390-394.
Hortelano et al., (1999). "Persistent Delivery of Factor IX in Mice: Gene Therapy for Hemophilia Using Implantable Microcapsules", Hum. Gene Ther., 10:1281-1288.
Huard et al. (1999), "Differentiation of Primary Myoblast Injection into the Lower Urinary Tract; Creation of Detrusor Cellular Myoplasty", J Urology, 161(4S)Supplement:66 (Abstract 248).
Huard et al., (1992). "Human Myoblast Transplantation: Preliminary Results of 4 cases", Muscle & Nerve, 15:550-560.
Huard et al., (1994). "High Efficiency of Muscle Regeneration after Human Myoblast Clone Transplantation in SCID Mice", J. Clin. Invest., 93:586-599.
Huard et al., (1994). "Human Myoblast Transplantation in Immunodeficient and Immunosuppressed Mice: Evidence of Rejection", Muscle & Nerve, 17:224-234.
Huard et al., (1995). "The route of administration is a major determinant of the transduction efficiency of rat tissues by adenoviral recombinants", Gene Therapy, 2:107-115.
Huard et al., (1998). "Myoblast Injection into the Bladder Wall: A Possible Method of Modulating Detrusor Contractility and Cell-Medicated Gene Therapy for Bladder Dysfunction", J. Urology, 159(5S)Supplement:16 (Abstract 62).
Huard et al., (1998). "Nitric oxide synthases (NOS) Gene Therapy for Erectile Dysfunction: Comparison Between Plasmid, Adenovirus and Adenovirus Transduced Myoblast Vectors", J. Urology, 159:90 (Abstract 342).
Huard et al., (2002). "Muscle-derived cell-mediated ex vivo gene therapy for urological dysfunction", Gene Ther., 9:1617-1626.
Ikada (2001), "Tissue Engineering—Toward Establishing of Basic Technology and Clinical Applications," Kagaku-Dojin Publishing Co., Inc. pp. 183-191. (Abstract only in English).
International Search Report and Written Opinion, Application No. PCT/US2008/011458, Date: Feb. 17, 2008.
Irintchev et al., (1994). "Expression Patter of M-Cadherin in Normal, Denervated, and Regenerating Mouse Muscles", Dev. Dynam., 199:326-337.
Jackson et al., (1999). "Hematopoietic potential of stem cells isolated from murine skeletal muscle", PNAS, 96(25):14482-14486.
Jankowski et al., (2001). "Flow Cytometric Characterization of Myogenic Cell Populations Obtained via the Preplate Technique: Potential for Rapid Isolation of Muscle-Derived Stem Cells", Human Gene Therapy, 12:619-628.
Japanese Office Action, Application No. JP2002-567239, Date: Feb. 7, 2007 (with English Translation).
Japanese Pre-Appeal Examination Report, Appl. No. JP2002-567239, Date: Oct. 22, 2007 (with English Translation).
Jiao et al., (1992). "Intracerebral transplants of primary muscle cells: a potential 'platform' for transgene expression in the brain", Brain Research, 575:143-147.
Jung et al., (1999). "Urethral Afferent Nerve Activity Affects the Micturition Reflex; Implication for the Relationship between Stress Incontinence and Detrusor Instability", J. Urology, 162(1):204-212.
Karpati et al., (1993). "Myoblast Transfer in Duchenne Muscular Dystrophy", Ann. Neurol., 34:8-17.
Kasemkijwattana et al., (1998). "Development of Approaches to Improve the Healing Following Muscle Contusion", Cell Transplantation, 7(6):585-598.
Katagiri et al., (1994). "Bone Morphogenetic Protein-2 Converts the Differentiation Pathway of C2C12 Myoblasts into the Osteoblast Lineage", J. Cell Biol., 127:1755-1766.
Koretzky (1993). "Role of the CD45 tyrosine phosphatase in signal transduction in the immune system", FASEB J., 7:420-426.

Kropp et al., (2000), "Bioengineering Organs Using Small Intestinal Submucosa Scaffolds: In Vivo Tissue-Engineering Technology", J. Endourology, 14(1):59-62.
Kuby (1994). "Transplantation Immunology", Immunology, 2nd Ed., WH Freeman Company, pp. 559-560.
Ledley (1996). "Pharmaceutical Approach to Somatic Gene Therapy", Pharmaceutical Research, 13(11):1595-1614.
Lee et al., (2000). "Clonal Isolation of Muscle-derived Cells Capable of Enhancing Muscle Regeneration and Bone Healing", J. Cell Biol., 150(5):1085-1099.
Lee et al., (2001). "Urethral Atrophy Incontinence Following Artificial Sphincter Placement: Is Cuff Downsizing Effective?", J. Urology (Suppl.), 165:254 (Abstract 1033).
Lipton et al., (1979). "Developmental Fate of Skeletal Muscle Satellite Cells", Science, 205:1292-1294.
Lynch et al., (1992). "Long-term expression of human adenosine deaminase in vascular smooth muscle cells of rats: A model for gene therapy", Proc. Natl. Acad. Sci. USA, 89:1138-1142.
Madeiro et al., (2002). "Effects of the association of androgen/estrogen on the bladder and urethra of castrated rats", Clin. Exp. Obst. & Gyn., XXIX(2):117-120.
Martini et al., (1995). "Integration with Other Systems", Anatomy and Physiology, 3rd Ed., Simon & Schuster Company, p. 315.
Miller et al., (1999). "Seeking Muscle Stem cells", Curr. Top. Dev. Biol., 43:191-219; see Table 3.
Moisset et al., (1998). "Successful Transplantation of Genetically Corrected DMD Myoblasts Following ex Vivo Transduction with the Dystrophin Minigene", Biochem. Biophys. Res. Commun., 247:94-99.
Moisset et al., (1998). "Expression of human dystrophin following the transplantation of genetically modified mdx myoblasts", Gene Ther., 5:1340-1346.
Morgan et al., (1988). "Partial correction of an inherited biochemical defect of skeletal muscle by grafts of normal muscle precursor cells", J Neural. Scie., 86:137-147.
Murry et al., (1996). "Skeletal Myoblast Transplantation for Repair of Myocardial Necrosis", J. Clin. Invest. 98:2512-2523.
Musgrave et al., (1998). "Muscle-based tissue engineering for the musculoskeletal system", Gene Therapy & Molecular Biology, 3:1-15.
Newman et al., (2003). "Stress Urinary Incontinence in Women", Am. J. Nurs., 103(8):46-55.
Nurcombe et al., (1985). "Motoneurone Survival and Neuritic Outgrowth Promoted by Different Cell Types in Embryonic Muscle", Developmental Brain Research, 21:49-60 (Abstract).
Osawa et al., (1996). "In Vivo Self-Renewal of c-Kit$^+$Sca-1$^+$Lin$^{low/-}$ Hemopoietic Stem Cells", J. Immunol., 156:3207-3214.
Partridge et al., (1978). "Evidence of fusion between host and donor myoblasts in skeletal muscle grafts", Nature, 73:306-308.
Partridge et al., (1989). "Conversion of mdx myofibers from dystrophin-negative to-positive by injection of normal myoblasts", Nature, 337:176-179.
Partridge & Davies, (1995). "Myoblast-based gene therapies", Brit. Med. Bulletin, 51:123-137.
Pittenger et al., (1999). "Multilineage Potential of Adult Human Mesenchymal Stem Cells", Science, 284:143-147.
Price et al., (1987). "Lineage analysis in the vertebrate nervous system by retrovirus-mediated gene transfer", Proc. Natl. Acad. Sci. USA, 84:156-160.
Qu et al., (1998). "Development of Approaches to Improve Cell Survival in Myoblast Transfer Therapy", J. Cell Biol., 142(5):1257-1267.
Qu et al., (1999). "Identification of muscle-derived stem cells", Molec. Biol. of the Cell, 10:246a.
Rando et al., (1994). "Primary Mouse Myoblast Purification, Characterization, and Transplantation for Cell-mediated Gene Therapy", J. Cell Biol., 125(6):1275-1287.
Regulier et al., (1998). "Continuous delivery of human and mouse erythropoietin in mice by genetically engineered polymer encapsulated myoblasts", Gene Ther., 5:1014-1022.
Richler et al., (1970). "The in Vitro Cultivation and Differentiation Capacities of Myogenic Cell Lines", Developmental Biology, 23:1-22.

(56) References Cited

OTHER PUBLICATIONS

Roman et al., (1992). "Circulating Human or Canine Factor IX from Retrovirally Transduced Primary Myoblasts and Established Myoblast Cell Lines Grafted into Murine Skeletal Muscle", Somat. Cell. Mol. Genet., 18:247-258.
Rosenberg et al., (2000). "Gene Therapist, Heal Thyself", Science, 287:1751.
Sanes et al., (1986). "Adult Stem Cells: The Therapeutic Potential of Skeletal Muscle", EMBO J. 5:3133.
Saini et al., (2006). "Use of a recombinant retrovirus to study post-implantation cell lineage in mouse embryos", Curr. Stem Cell Res. Ther. 1(2):157-171.
Seale et al., (2000). "A New Look at the Origin, Function, and 'Stem-Cell' Status of Muscle Satellite Cells", Developmental Biology, 218:115-124.
Simmons et al., (1991). "CD34 Expression by Stromal Precursors in Normal Human Adult Bone Marrow", Blood, 78:2848-2853.
Smith et al., (1997). "Stable Integration of an mdx Skeletal Muscle Cell Line into Dystrophic (mdx) Skeletal Muscle: Evidence for Stem Cell Status", Cell Growth and Differentiation, 8(8):927-934.
Somogyi et al., (1999). "A precise, localized bladder injury model to investigate the effect of myoblast injection on bladder contractility", J Urology, 161(4S)Supplement:43 (Abstract 158).
Spindler et al., (1995). "Regional Mitogenic Response of the Meniscus to Platelet-Derived Growth Factor (PDGF-AB)", J. of Orthopedic Research, 13:201-207.
Tirney et al., (1998), "Nitric Oxide Synthase Gene Therapy for Erectile Dysfunction: Comparison of Plasmid, Adenovirus, and Adenovirus-Transduced Myoblast Vectors", J Urology, 159(5S)Supplement:327 (Abstract 1256).
Tirney et al., (2001). "Myoblast Periuretheral Injection for the Treatment of Stress Urinary Incontinence", Mol. Urol. Spring, 5(1):37-43.
Tremblay et al., (1993). "Results of triple blind clinical study of myoblast transplantations without immunosuppressive treatment in young boys with Duchenne muscular dystrophy", Cell Transplantation, 2:99-112.
Tremblay et al., (1997). "Myoblast Transplantation: a Brief Review of the Problems and of Some Solutions", Basic Appl. Myol., 7(3 &4):221-230.
Tzeng et al., (1996). "Vascular inducible nitric oxide synthase gene therapy: Requirement for guanosine triphosphate cyclohydrolase I", Surgery, 120(2):315-321.
Van De Rijn et al., (1989). "Mouse hematopoietic stem-cell antigen Sca-1 is a member of the Ly-6 antigen family", Proc. Natl. Acad. Sci. USA, 86:4634-4638.
Vandenburgh (1996). "Tissue-Engineered Skeletal Muscle Organoids for Reversible Gene Therapy", Hum. Gene Ther., 7:2195-2200.
Verma (2000). "Gene Therapy: Beyond 2000", Mol. Ther., 1:493.
Wang et al., (1997). "Persistent Systemic Production of Human Factor IX in Mice by Skeletal Myoblast-Mediated Gene Transfer: Feasibility of Repeat Application to Obtain Therapeutic Levels", Blood, 90:1075-1082.
Watt et al., (1984). "Long term survival of allografted muscle precursor cells following a limited period of treatment with cyclosporin A", Clin. Exp. Immunol., 55:419-426.
Webster et al., (1988). "Isolation of Human Myoblasts with the Fluorescence-Activated Cell Sorter", Exp. Cell. Res., 174:252-265.
Yamanishi et al., (2002). "Identification of Beta-Adrenoceptor Subtypes in Lower Urinary Tract of the Female Pig", J. Urology, 168:2706-2710.
Yao et al., (1994). "Primary myoblast-mediated gene transfer: persistent expression of human factor IX in mice", Gene Ther., 1:99-107.
Yokoyama et al. (1999), "Primary Myoblast Injection into the Urethra and Bladder as a Potential Treatment of Stress Urinary Incontinence and Impaired Detrusor Contractility; Long-Term Survival Without Significant Cytotoxicity", J Urology, 161(4S)Supplement:307 (Abstract 1182).
Yokoyama et al., (1999). "Gene therapy as a potential treatment for BPH: Injection of myoblast-adenovirus transfected with human inducible nitric oxide synthase (iNOS) into the proximal urethra", J. Urology, 161(4S)Supplement:305 (Abstract 1775).
Yokoyama et al., (2000). "Myoblast therapy for stress urinary incontinence and bladder dysfunction", World J. Urology, 18:56-61.
Yokoyama et al., (2001). "Persistence and Survival of Autologous Muscle Derived Cells Versus Bovine Collagen as Potential Treatment of Stress Urinary Incontinence", J. Urology, 165:271-276.
Yokoyama et al., (2001). "Muscle-derived cell transplantation and differentiation into lower urinary tract smooth muscle", Tissue Engineering, 7(4):395-404.
Yokoyama et al., (2001). "Autologous Primary Muscle-Derived Cells Transfer into the Lower Urinary Tract", Urology, 57(4):826-831.
Yoshida et al., (1998). "Cell heterogeneity upon myogenic differentiation: Down-regulation of MyoD and Myf-5 generates reserve cells", J. Cell Science. 111:769-779.
Young et al., (1993). "Pluripotent mesenchymal stem cells reside within avian connective tissue matrices", In vitro Cell Dev. Biol., 29A:723-736.
Young et al., (1995). "Mesenchymal Stem Cells Reside Within the Connective Tissues of Many Organs", Dev. Dynam., 202:137-144.
Ziegler et al., (1999). "KDR Receptor: A Key Marker Defining Hematopoietic Stem Cells", Science, 285:1533-1558.
Mastrogiacomo M. et al., "Bone and Cartilage Formation by Skeletal Muscle Derived Cells" *J. Cell. Physiol.*, 204(2):594-603 (2005).
Sun et al. "The Role of Muscle-derived Stem Cells in Bone Tissue Engineering" *Biomaterials*, 26(18):3953-3960 (2005).
Adachi et al., "Muscle derived, cell based ex vivo gene therapy for treatment of full thickness articular cartilage defects", *J. Rheumatol.*, 29(9):1920-1930 (2002).
Kaufman et al. (1988), PNAS, 85:9606-9610.
Office Action issued for U.S. Appl. No. 11/505,735, Mail Date: Sep. 9, 2009.
Berjukow et al., "Membrane properties of single muscle cells of the rhabdosphincter of the male urethra", Prostate (2004), 58(3): 238-247.
Torrente et al. (2001), "Intraarterial Injection of Muscle-derived CD34±Sca-;1+ Stem Cells Restores Dystrophin in mdx Mice", J of Cell Biology, 152(2):335-348.
Crisan et al., "Identification, purification and characterization of a novel population of cd146+cd133+ myogenic cells in human skeletal muscle", The Orthopaedic Research Society (ORS) 53rd Annual Meeting (Feb. 12-14, 2007), San Diego, CA (Paper No. 0040).
Ding et al., "Bone marrow stromal cells as a vehicle for gene transfer", Gene Therapy (1999), 6(9):1611-1616.
Deasy et al., "A role for cell sex in stem cell mediated skeletal muscle regeneration: female cells have higher muscle regeneration efficiency", J. Cell Biol. (2007), 177(1):73-86.
Oshima et al., "Skeletal muscle stem cells acquire a cardiac phenotype and display a superior ability for cardiac repair when compared to satellite cells", The Japanese Journal of Thoracic and Cardiovascular Surgery, 52(Suppl 2004):192.
Oshima et al., "Muscle stem cells provide superior infarct repair when compared with myoblasts", Molecular Therapy (2005), 11(Suppl 1):920.
Oshima et. al., "Differential myocardial infarct repair with muscle stem cells compared to myoblasts", Mol. Ther. (2005), 12(6):1130-41.
Payne et al., "Muscle-derived stem cells express a cardiac phenotype upon transplantation into the dystrophic murine heart", American Heart Association Conference on Molecular Mechanisms of Growth, Death and Regeneration in the Myocardium (Aug. 2003), Snowbird, UT, 9: p. 42.
Payne et. al., "Regeneration of dystrophin-expressing myocytes in the mdx heart by skeletal muscle stem cells", Gene Ther. (2005), 12(16):1264-74.
Payne et al., "A relationship between VEGF, angiogenesis and cardiac repair after muscle stem cell transplantation into ischemic hearts", Journal of the American College of Cardiology (2007), 50(17):1677-84.
Payne et al., "VEGF secretion by skeletal muscle-derived stem cells induces neovascularization, prevents remodeling, and improves function in ischemic heart", Circulation Research (2006), 99(5):p. 17.

(56) References Cited

OTHER PUBLICATIONS

Payne et al., "Muscle stem cells deliver dystrophin and adopt a cardiac phenotype through both differentiation and fusion in the dystrophic (mdx) heart", Mol Ther (2004), 9(Suppl 1):930.
Payne et al., "Muscle stem cells genetically modified to express a VEGF antagonist display an impaired ability for cardiac repair", Mol Ther (2005), 11(Suppl 1):923.
Urish et al., "Muscle stem cells' high regenerative capacity correlates with a high resistance to stress", The Orthopaedic Research Society 52nd Annual Meeting (Mar. 19-22, 2006), Chicago, IL (Paper No. 0337).
Urish et al.,"The role of resistance to inflammation and oxidative stress in muscle stem cells' increased regenerative capacity", International Society for Stem Cell Research (Jun. 29-Jul. 1, 2006), Toronto, Canada.
Urish et al., "Oxidative stress plays a major role in the differential repair of skeletal and cardiac muscle between muscle stem cells and myoblasts", The Orthopaedic Research Society (ORS) 53rd Annual Meeting (Feb. 12-14, 2007), San Diego, CA (Paper No. 1225).
Zheng et al., "Multi-potency of myo-endothelial clones isolated from adult human skeletal muscle. NIRA nominee", The Orthopaedic Research Society (ORS) 53rd Annual Meeting (Feb. 12-14, 2007), San Diego, CA (Paper No. 0421).
Rando et al. "Methods for Myoblast Transplantation." *Meth. Cell Biol.* 52(1998):261-272.
"Desmin." *Wikipedia: The Free Encyclopedia.* Wikimedia Foundation, Inc., Web. Nov. 17, 2012. http://en.wikipedia.org/wiki/Desmin.
Andersson et al. "Advances in the Pharmacological Control of the Bladder." *Exp. Physiol.* 84(1999):195-213.
Dixon et al. "Recombinant Human Bone Morphogenetic Proteins-2 and -4 Induce Several Mesenchymal Phenotypes in Culture." *Wound Rep. Reg.* 4(1996):374-380.
Jancel et al. "Management of Uncomplicated Urinary Tract infections." *West J. Med.* 176(2002):51-55.
"Your Urinary System and How it Works." *National Kidney and Urologic Diseases Information Clearinghouse.* NIH Publication No. 07-3195, 2007.
Abraham et al. "Evaluation of the Porcine Intestinal Collagen Layer as a Biomaterial." *J. Biomed. Mat. Res.* 51.3(2000):442-452.
Auger et al. "Tissue-Engineered Human Skin Substitutes Developed from Collagen-Populated Hydrated Gels: Clinical and Fundamental Applications." *Med. Biol. Eng. Comput.* 36(1998):801-812.
Baltoyannis et al. "Submucosa of Canine Small Intestine as an Alternative Medium-Diameter Autogenous Arterial Graft." *Int. Angiol.* 19.3(2000):280-284.
Berman et al. "Comparative Cost Analysis of Collagen Injection and Fascia Lata Sling Cystourethropexy for the Treatment of Type III Incontinence in Women." *J. Urol.* 157(1997):122-124.
Berthod et al. "Collagen Synthesis by Fibroblasts Cultured with a Collagen Sponge." *Biomat.* 14.10(1993):749-754.
Berthod et al. "In vitro reconstructed Skin Models for Wound Coverage in Deep Burns." *Brit. J. Dermatol.* 136(1997):809-816.
Boyce. "Cultured Skin Substitutes: A Review." *Tissue Eng.* 2.4(1996):255-266.
Cossu et al. "New Therapies for Muscular Dystrophy: Cautious Optimism." *Trends Mol. Med.* 10.10(2004):516-520.
Game et al. "Rejection Mechanisms in Transplantation." *Wien Klin Wochenschr.* 113(2001):823-838.
Gao et al. "The Dynamic in vivo Distribution of Bone Marrow-Derived Mesenchymal Stem Cells after Infusion." *Cells Tissues Organs.* 169(2001):12-20.
Germain et al. "Tissue Engineering of the Vascular System: From Capillaries to Larger Blood Vessels." *Med. Biol. Eng. Comput.* 38(2000):232-240.
Goldring et al. "Clinical Aspects, Pathology and Pathophysiology of Osteoarthritis." *J. Musculoskelet. Neuronal Interact.* 6.4(2006):376-378.
Goldring. "Are Bone Morphogenetic Proteins Effective Inducers of Cartilage Repair? Ex Vivo Transduction of Muscle-Derived Stem Cells." *Arthritis Rheum.* 54.2(2006):387-389.
Grinnell. "Trophic Interaction Between Nerve and Muscle." *Myology.* Engel et al., eds. New York: McGraw-Hill, Inc. 2(1994):303-332.
Hansbrough et al. "Evalution of a Biodegradable Matrix Containing Cultured Human Fibroblasts as a Dermal Replacement Beneath Meshed Skin Grafts on Athymic Mice." *Surg.* 111.1(1992):438-446.
Irintchev et al. "Ectopic Skeletal Muscles Derived from Myoblasts Implanted Under the Skin." *J. Cell Sci.* 111(1998):3287-3297.
Kropp et al. "Regenerative Urinary Bladder Augmentation Using Small Intestinal Submucosa: Urodynamic and Histopathologic Assessment in Long-Term Canine Bladder Augmentations." *J. Urol.* 155(1996):2098-2104.
Langer et al. "Tissue Engineering." *Science.* 260(1993):920-926.
Lucas et al. "Effect of Rat Mesenchymal Stem Cells on Development of Abdominal Adhesions After Surgery." *J. Surg. Res.* 62.2(1996):229-232.
Mak et al. "Injectable Filler Materials for Soft-Tissue Augmentation." *Otolaryngol. Clin. North Am.* 27.1(1994):211-222.
Menasché. "Skeletal Myoblasts as a Therapeutic Agent." *Prog. Cardiovasc. Dis.* 50.1(2007):7-17.
Minuth et al. "Tissue Engineering: Generation of Differentiated Artificial Tissues for Biomedical Applications." *Cell Tissue Res.* 291(1998):1-11.
Mouly et al. "Myoblast Transfer Therapy: Is There any Light at the End of the Tunnel?" *Acta Myol.* 24.2(2005):128-133.
Naughton et al. "Human-Based Tissue Engineered Implants for Plastic and Reconstructive Surgery." *Clin. Plastic Surg.* 26.4(1999):579-586.
Odorico et al. "Multilineage Differentiation from Human Embryonic Stem Cell Lines." *Stem Cells.* 19(2001):193-204.
Platt et al. "Knocking Out Xenograft Rejection." *Nat. Biotech.* 20.3(2002):231-232.
Shapiro et al. "Novel Alginate Sponges for Cell Culture and Transplantation." *Biomat.* 18.8(1997):583-590.
van Wachem et al. "Myoblast Seeding in a Collagen Matrix Evaluated in vitro." *J. Biomed. Mat. Res.* 30(1996):353-360.
Watt et al. "Out of Eden: Stem Cells and Their Niches." *Science.* 287(2000):1427-1430.
Ye et al. "Tissue Engineering in Cardiovascular Surgery: New Approach to Develop Completely Human Autologous Tissue." *Eur. J. Cardio-Thorac. Surg.* 17(2000):449-454.
Young et al. "Use of Mesenchymal Stem Cells in a Collagen Matrix for Achilles Tendon Repair." *J. Orthop. Res.* 16.4(1998):406-413.
Zhang et al. "Coculture of Bladder Urothelial and Smooth Muscles Cells on Small Intestinal Submucosa: Potential Applications for Tissue Engineering Technology." *J. Urol.* 164(2000):928-935.

\* cited by examiner

BONE AUGMENTATION UTILIZING MUSCLE-DERIVED PROGENITOR COMPOSITIONS IN BIOCOMPATIBLE MATRIX, AND TREATMENTS THEREOF

RELATED APPLICATIONS

This application claims priority from U.S. Provisional Patent Applications 61/089,798, filed on Aug. 18, 2008 and 61/166,775, filed on Apr. 6, 2009, incorporated by reference, herein, in their entireties.

GOVERNMENT INTERESTS

This invention was made with Government support under Grant No. R01-DE13420-01 awarded by the National Institutes of Health. The Government has certain rights in this invention.

FIELD OF THE INVENTION

The present invention relates to muscle-derived progenitor cells (MDCs) and compositions of MDCs with biologically compatible matrix and their use with the augmentation of body tissues, particularly bone. In particular, the present invention relates to muscle-derived progenitor cells that show long-term survival following introduction into bone used in combination with small intestine sub-mucosa for the augmentation of human or animal bone. The invention also relates to novel uses of muscle-derived progenitor cells with biologically compatible matrix for the treatment of cosmetic or functional conditions, such as osteoporosis, Paget's Disease, osteogenesis imperfecta, bone fracture, osteomalacia, decrease in bone trabecular strength, decrease in bone cortical strength and decrease in bone density with old age. The invention also relates to the novel use of MDCs with biologically compatible matrix for the increase of bone mass in athletes or other organisms in need of greater than average bone mass.

BACKGROUND OF THE INVENTION

Myoblasts, the precursors of muscle fibers, are mononucleated muscle cells that fuse to form post-mitotic multinucleated myotubes, which can provide long-term expression and delivery of bioactive proteins (T. A. Partridge and K. E. Davies, 1995, Brit. Med. Bulletin 51:123 137; J. Dhawan et al., 1992, Science 254: 1509 12; A. D. Grinnell, 1994, Myology Ed 2, A. G. Engel and C. F. Armstrong, McGraw-Hill, Inc., 303 304; S. Jiao and J. A. Wolff, 1992, Brain Research 575:143 7; H. Vandenburgh, 1996, Human Gene Therapy 7:2195 2200).

Cultured myoblasts contain a subpopulation of cells that show some of the self-renewal properties of stem cells (A. Baroffio et al., 1996, Differentiation 60:47 57). Such cells fail to fuse to form myotubes, and do not divide unless cultured separately (A. Baroffio et al., supra). Studies of myoblast transplantation (see below) have shown that the majority of transplanted cells quickly die, while a minority survive and mediate new muscle formation (J. R. Beuchamp et al., 1999, J. Cell Biol. 144:1113 1122). This minority of cells shows distinctive behavior, including slow growth in tissue culture and rapid growth following transplantation, suggesting that these cells may represent myoblast stem cells (J. R. Beuchamp et al., supra).

Myoblasts have been used as vehicles for gene therapy in the treatment of various muscle- and non-muscle-related disorders. For example, transplantation of genetically modified or unmodified myoblasts has been used for the treatment of Duchenne muscular dystrophy (E. Gussoni et al., 1992, Nature, 356:435 8; J. Huard et al., 1992, Muscle & Nerve, 15:550 60; G. Karpati et al., 1993, Ann. Neurol., 34:8 17; J. P. Tremblay et al., 1993, Cell Transplantation, 2:99 112; P. A. Moisset et al., 1998, Biochem. Biophys. Res. Commun. 247: 94 9; P. A. Moisset et al., 1998, Gene Ther. 5:1340 46). In addition, myoblasts have been genetically engineered to produce proinsulin for the treatment of Type 1 diabetes (L. Gros et al., 1999, Hum. Gen. Ther. 10:1207 17); Factor IX for the treatment of hemophilia B (M. Roman et al., 1992, Somat. Cell. Mol. Genet. 18:247 58; S. N. Yao et al., 1994, Gen. Ther. 1:99 107; J. M. Wang et al., 1997, Blood 90:1075 82; G. Hortelano et al., 1999, Hum. Gene Ther. 10:1281 8); adenosine deaminase for the treatment of adenosine deaminase deficiency syndrome (C. M. Lynch et al., 1992, Proc. Natl. Acad. Sci. USA, 89:1138 42); erythropoietin for the treatment of chronic anemia (E. Regulier et al., 1998, Gene Ther. 5:1014 22; B. Dalle et al., 1999, Gene Ther. 6:157 61), and human growth hormone for the treatment of growth retardation (K. Anwer et al., 1998, Hum. Gen. Ther. 9:659 70).

Myoblasts have also been used to treat muscle tissue damage or disease, as disclosed in U.S. Pat. No. 5,130,141 to Law et al., U.S. Pat. No. 5,538,722 to Blau et al., and application U.S. Ser. No. 09/302,896 filed Apr. 30, 1999 by Chancellor et al. In addition, myoblast transplantation has been employed for the repair of myocardial dysfunction (C. E. Murry et al., 1996, J. Clin. Invest. 98:2512 23; B. Z. Atkins et al., 1999, Ann. Thorac. Surg. 67:124 129; B. Z. Atkins et al., 1999, J. Heart Lung Transplant. 18:1173 80).

In spite of the above, in most cases, primary myoblast-derived treatments have been associated with low survival rates of the cells following transplantation due to migration and/or phagocytosis. To circumvent this problem, U.S. Pat. No. 5,667,778 to Atala discloses the use of myoblasts suspended in a liquid polymer, such as alginate. The polymer solution acts as a matrix to prevent the myoblasts from migrating and/or undergoing phagocytosis after injection. However, the polymer solution presents the same problems as the biopolymers discussed above. Furthermore, the Atala patent is limited to uses of myoblasts in only muscle tissue, but no other tissue.

Thus, there is a need for other, different tissue augmentation materials that are long-lasting, compatible with a wide range of host tissues, and which cause minimal inflammation, scarring, and/or stiffening of the tissues surrounding the implant site. Accordingly, the muscle-derived progenitor cell (MDC)-containing compositions of the present invention are provided as improved and novel materials for augmenting bone. Further provided are methods of producing muscle-derived progenitor cell compositions that show long-term survival following transplantation, and methods of utilizing MDCs and compositions containing MDCs to treat various aesthetic and/or functional defects, including, for example osteoporosis, Paget's Disease, osteogenesis imperfecta, bone fracture, osteomalacia, decrease in bone trabecular strength, decrease in bone cortical strength and decrease in bone density with old age. Also provided are methods of using MDCs and compositions containing MDCs for the increase of bone mass in athletes or other organisms in need of greater than average bone mass.

It is notable that prior attempts to use myoblasts for non-muscle tissue augmentation were unsuccessful (U.S. Pat. No. 5,667,778 to Atala). Therefore, the findings disclosed herein are unexpected, as they show that the muscle-derived progenitor cells according to the present invention can be successfully transplanted into non-muscle tissue, including bone tissue, and exhibit long-term survival. As a result, MDCs and compositions comprising MDCs can be used as a general augmentation material for bone production. Moreover, since the muscle-derived progenitor cells and compositions of the present invention can be derived from autologous sources, they carry a reduced risk of immunological complications in the host, including the reabsorption of augmentation materials, and the inflammation and/or scarring of the tissues surrounding the implant site.

Although mesenchymal stem cells can be found in various connective tissues of the body including muscle, bone, cartilage, etc. (H. E. Young et al., 1993, In vitro Cell Dev. Biol. 29A:723 736; H. E. Young, et al., 1995, Dev. Dynam. 202:137 144), the term mesenchymal has been used historically to refer to a class of stem cells purified from bone marrow, and not from muscle. Thus, mesenchymal stem cells are distinguished from the muscle-derived progenitor cells of the present invention. Moreover, mesenchymal cells do not express the CD34 cell marker (M. F. Pittenger et al., 1999, Science 284:143 147), which is expressed by the muscle-derived progenitor cells described herein.

SIS is an acellular, naturally occurring collagenous extracellular matrix material derived from the submucosa of porcine small intestine, which contains bioactive molecules (TGF-$\beta$, bFGF) (Voytik-Harbin S, et al. J Cell Biochem, 1997). While SIS is primarily used for the repair of soft tissues, its potential as a bone graft material is still under debate. Only a few studies reported that SIS had potential for bone regeneration (Suckow M, et al. J Invest Surg, 1999, Voytik-Harbin S, et al. Trans First SIS Symposium, 1996). Most recent report from Moore D, et al. J Biomed Mater Res, 2004 suggests that SIS is not capable of inducing or conducting new bone formation across a critical size segmental bone defect.

Moreover, current methods of producing cell matrices for in vivo tissue and organ repair are very costly and time consuming. Such cell matrices are costly due to the specialized factories and/or procedures needed to produce these products. Also, since cell-matrix products involve living biological cells/tissue, a tremendous loss of product occurs from shipping, the delays associated therewith, and the like. Additionally, given the nature of the products, obtaining regulatory approval for new products that are based on living cells and a new matrix poses difficulties.

Thus, there is a serious need for cell-matrix compositions that are low in cost, that are versatile, and easily prepared and/or manufactured. There is a further need for cell matrix compositions that do not require extensive in vitro incubation or cultivation periods after the cells have been incorporated into the matrix. Those in the art have recognized that a major problem remaining to be solved is the delay in producing the cell-matrix product after initial preparation. Specifically, it has been stated that there is a problem of a three week delay necessary to produce a sufficient amount of autologous keratinocytes and fibroblasts for the production of reconstructed skin. (F. Berthod and O. Damour, 1997, British Journal of Dermatology, 136: 809-816). The present invention provides a solution for the above-mentioned problems and delays currently extant in the art.

The description herein of disadvantages and problems associated with known compositions, and methods is in no way intended to limit the scope of the embodiments described in this document to their exclusion. Indeed, certain embodiments may include one or more known compositions, compounds, or methods without suffering from the so-noted disadvantages or problems.

SUMMARY OF THE INVENTION

It is an object of the present invention to provide uses for MDCs and compositions comprising MDCs with biologically compatible matrix for the augmentation of non-muscle tissue, including bone, without the need for polymer carriers or special culture media for transplantation. Such uses include the administration of MDC compositions with biologically compatible matrix by introduction into bone, for example by direct injection into or on the surface of the tissue, wherein the tissue as been previously administered a biologically compatible matrix. Preferably, this matrix is small intestine submucosa (SIS).

It is yet another object of the present invention to provide uses for MDCs for augmenting bone, following injury, wounding, surgeries, traumas, non-traumas, or other procedures that result in fissures, openings, depressions, wounds, and the like.

The invention provides the use of SIS seeded with MDCs for treating a bone disease, defect or pathology or improving at least one symptom associated with a bone disease, defect or pathology in a mammalian subject in need thereof wherein the MDCs are isolated from skeletal muscle, wherein the MDCs express desmin and wherein the MDCs are able to form bone tissue. In one embodiment, the MDC seeded SIS is administered by applying it to the surface of the bone. In another embodiment, the MDC seeded SIS is positioned in the interior of the bone. In another embodiment, the mammal is a human. In some embodiments, the symptom is selected from the group consisting of decreased bone density and decreased bone mass.

In another specific embodiment, the MDCs are cultured to expand their number before being used to seed the SIS. Preferably, the MDCs are frozen to a temperature below $-30°$ C. after being cultured to expand their number and thawed prior to being used to seed SIS.

In another embodiment, the skeletal muscle cells are isolated from the human subject before the bone disease, defect or pathology begins in the human subject. Preferably, when the bone defect, disease or pathology is a bone defect the bone defect is a bone fracture caused by trauma.

In other preferred embodiments, the MDCs are isolated by a method comprising: isolating skeletal muscle cells from a mammal, suspending the mammalian skeletal muscle cells in a first cell culture container for between 30 and 120 minutes; decanting the media from the first cell culture container to a second cell culture container; allowing the remaining cells in the media to attach to the walls of the second cell culture container; isolating the cells from the walls of the second cell culture container, wherein the isolated cells are MDCs; providing small intestine submucosa (SIS); seeding the SIS with MDCs; and administering the MDC seeded SIS to a bone suffering from the bone defect, disease or pathology of the mammalian subject.

Preferably, the mammalian skeletal muscle cells are cooled to a temperature below $10°$ C. and stored for 1-7 days after being isolated and before being suspended in a first cell culture container between 30 and 120 minutes In other preferred embodiments, the MDCs are isolated by a method comprising: plating a suspension of skeletal muscle cells from mammalian skeletal muscle tissue in a first container to which fibroblast cells of the skeletal muscle cell suspension adhere, re-plating non-adherent cells from step (a) in a second container, wherein the step of re-plating is after 15-20% of cells have adhered to the first container; repeating step (b) at least once; and isolating the non-adherent cells wherein the isolated cells are MDCs; providing small intestine submucosa (SIS); seeding the SIS with MDCs; and administering the MDC seeded SIS to a bone suffering from the bone defect, disease or pathology of the mammalian subject.

Additional objects and advantages afforded by the present invention will be apparent from the detailed description and exemplification hereinbelow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The appended drawings of the figures are presented to further describe the invention and to assist in its understanding through clarification of its various aspects.

DETAILED DESCRIPTION OF THE INVENTION

Figure 1:
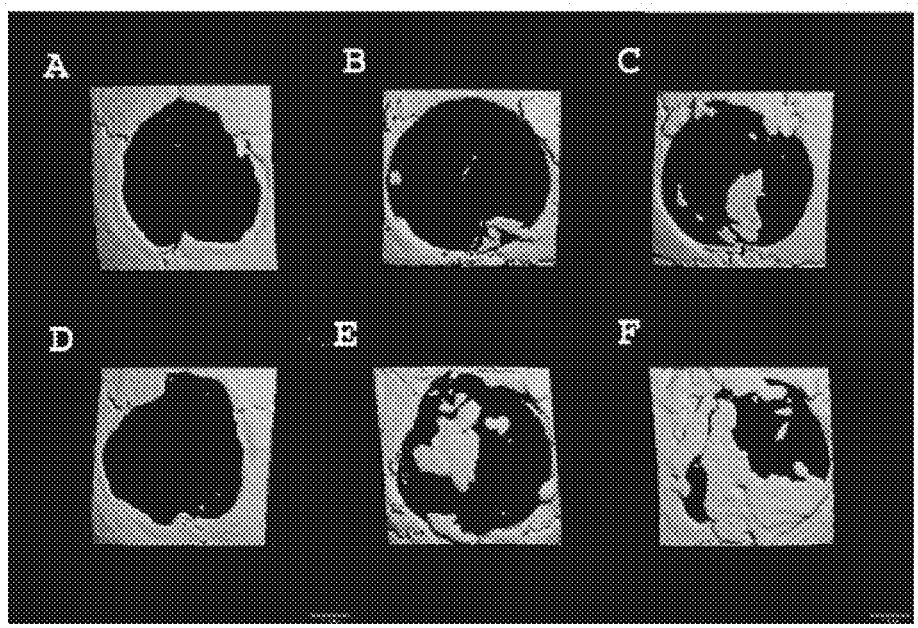
FIG. 1 shows 3D reconstruction of untreated (A,D), SIS-treated (B,E) and SIS-hMDC-treated (C,F) calvarial defects at 4 weeks (A,B,C) and 10 weeks (D,E,F) after surgery.

The invention provides methods of treating bone disorders including incontinence osteoporosis, Paget's Disease, osteogenesis imperfecta, bone fracture, osteomalacia, decrease in bone trabecular strength, decrease in bone cortical strength and decrease in bone density with old age. The isolation of human muscle-derived cells (MDCs) from adult tissue are capable of achieving increased bone density and bone volume within human subjects administered these cells in combination with a biologically compatible matrix.

Muscle-Derived Cells and Compositions

The present invention provides MDCs comprised of early progenitor cells (also termed muscle-derived progenitor cells or muscle-derived stem cells herein) that show long-term survival rates following transplantation into body tissues, preferably bone. To obtain the MDCs of this invention, a muscle explant, preferably skeletal muscle, is obtained from an animal donor, preferably from a mammal, including humans. This explant serves as a structural and functional syncytium including "rests" of muscle precursor cells (T. A. Partridge et al., 1978, Nature 73:306 8; B. H. Lipton et al., 1979, Science 205:12924).

Cells isolated from primary muscle tissue contain mixture of fibroblasts, myoblasts, adipocytes, hematopoietic, and muscle-derived progenitor cells. The progenitor cells of a muscle-derived population can be enriched using differential adherence characteristics of primary muscle cells on collagen coated tissue flasks, such as described in U.S. Pat. No. 6,866,842 of Chancellor et al. Cells that are slow to adhere tend to be morphologically round, express high levels of desmin, and have the ability to fuse and differentiate into multinucleated myotubes U.S. Pat. No. 6,866,842 of Chancellor et al.). A subpopulation of these cells was shown to respond to recombinant human bone morphogenic protein 2 (rhBMP-2) in vitro by expressing increased levels of alkaline phosphatase, parathyroid hormone dependent 3',5'-cAMP, and osteogenic lineage and myogenic lineages (U.S. Pat. No. 6,866,842 of Chancellor et al.; T. Katagiri et al., 1994, J. Cell Biol., 127: 1755 1766).

In one embodiment of the invention, a preplating procedure may be used to differentiate rapidly adhering cells from slowly adhering cells (MDCs). In accordance with the present invention, populations of rapidly adhering MDC (PP1-4) and slowly adhering, round MDC (PP6) were isolated and enriched from skeletal muscle explants and tested for the expression of various markers using immunohistochemistry to determine the presence of pluripotent cells among the slowly adhering cells (Example 1; patent application U.S. Ser. No. 09/302,896 of Chancellor et al.). As shown in Table 2, Example 3 herein, the PP6 cells expressed myogenic markers, including desmin, MyoD, and Myogenin. The PP6 cells also expressed c-met and MNF, two genes which are expressed at an early stage of myogenesis (J. B. Miller et al., 1999, Curr. Top. Dev. Biol. 43:191 219; see Table 3). The PP6 showed a lower percentage of cells expressing M-cadherin, a satellite cell-specific marker (A. Irintchev et al., 1994, Development Dynamics 199:326 337), but a higher percentage of cells expressing Bcl-2, a marker limited to cells in the early stages of myogenesis (J. A. Dominov et al., 1998, J. Cell Biol. 142:537 544). The PP6 cells also expressed CD34, a marker identified with human hematopoietic progenitor cells, as well as stromal cell precursors in bone marrow (R. G. Andrews et al., 1986, Blood 67:842 845; C. I. Civin et al., 1984, J. Immunol. 133:157 165; L. Fina et al, 1990, Blood 75:2417 2426; P. J. Simmons et al., 1991, Blood 78:2848 2853; see Table 3). The PP6 cells also expressed Flk-1, a mouse homologue of human KDR gene which was recently identified as a marker of hematopoietic cells with stem cell-like characteristics (B. L. Ziegler et al., 1999, Science 285:1553 1558; see Table 3). Similarly, the PP6 cells expressed Sca-1, a marker present in hematopoietic cells with stem cell-like characteristics (M. van de Rijn et al., 1989, Proc. Natl. Acad. Sci. USA 86:4634 8; M. Osawa et al., 1996, J. Immunol. 156:3207 14; see Table 3). However, the PP6 cells did not express the CD45 or c-Kit hematopoietic stem cell markers (reviewed in L K. Ashman, 1999, Int. J. Biochem. Cell. Biol. 31:1037 51; G. A. Koretzky, 1993, FASEB J. 7:420 426; see Table 3).

In one embodiment of the present invention is the PP6 population of muscle-derived progenitor cells having the characteristics described herein. These muscle-derived progenitor cells express the desmin, CD34, and Bcl-2 cell markers. In accordance with the present invention, the PP6 cells are isolated by the techniques described herein (Example 1) to obtain a population of muscle-derived progenitor cells that have long-term survivability following transplantation. The PP6 muscle-derived progenitor cell population comprises a significant percentage of cells that express progenitor cell markers such as desmin, CD34, and Bcl-2. In addition, PP6 cells express the Flk-1 and Sca-1 cell markers, but do not express the CD45 or c-Kit markers. Preferably, greater than 95% of the PP6 cells express the desmin, Sca-1, and Flk-1 markers, but do not express the CD45 or c-Kit markers. It is preferred that the PP6 cells are utilized within about 1 day or about 24 hours after the last plating.

In a preferred embodiment, the rapidly adhering cells and slowly adhering cells (MDCs) are separated from each other using a single plating technique. One such technique is described in Example 2. First, cells are provided from a skeletal muscle biopsy. The biopsy need only contain about 100 mg of cells. Biopsies ranging in size from about 50 mg to about 500 mg are used according to both the pre-plating and single plating methods of the invention. Further biopsies of 50, 100, 110, 120, 130, 140, 150, 200, 250, 300, 400 and 500 mg are used according to both the pre-plating and single plating methods of the invention.

In a preferred embodiment of the invention, the tissue from the biopsy is then stored for 1 to 7 days. This storage is at a temperature from about room temperature to about 4° C. This waiting period causes the biopsied skeletal muscle tissue to undergo stress. While this stress is not necessary for the isolation of MDCs using this single plate technique, it seems that using the wait period results in a greater yield of MDCs.

According to preferred embodiments, tissue from the biopsies is minced and centrifuged. The pellet is resuspended and digested using a digestion enzyme. Enzymes that may be used include collagenase, dispase or combinations of these enzymes. After digestion, the enzyme is washed off of the cells. The cells are transferred to a flask in culture media for the isolation of the rapidly adhering cells. Many culture media may be used. Particularly preferred culture media include those that are designed for culture of endothelial cells including Cambrex Endothelial Growth Medium. This medium may be supplemented with other components including fetal bovine serum, IGF-1, bFGF, VEGF, EGF, hydrocortisone, heparin, and/or ascorbic acid. Other media that may be used in the single plating technique include InCell M310F medium. This medium may be supplemented as described above, or used unsupplemented.

The step for isolation of the rapidly adhering cells may require culture in flask for a period of time from about 30 to about 120 minutes. The rapidly adhering cells adhere to the flask in 30, 40, 50, 60, 70, 80, 90, 100, 110 or 120 minutes. After they adhere, the slowly adhering cells are separated from the rapidly adhering cells from removing the culture media from the flask to which the rapidly adhering cells are attached to.

The culture medium removed from this flask is then transferred to a second flask. The cells may be centrifuged and resuspended in culture medium before being transferred to the second flask. The cells are cultured in this second flask for between 1 and 3 days. Preferably, the cells are cultured for two days. During this period of time, the slowly adhering cells (MDCs) adhere to the flask. After the MDCs have adhered, the culture media is removed and new culture media is added so that the MDCs can be expanded in number. The MDCs may be expanded in number by culturing them for from about 10 to about 20 days. The MDCs may be expanded in number by culturing them for 10, 11, 12, 13, 14, 15, 16, 17, 18, 19 or 20 days. Preferably, the MDCs are subject to expansion culture for 17 days.

As an alternative to the pre-plating and single plating methods, the MDCs of the present invention can be isolated by fluorescence-activated cell sorting (FACS) analysis using labeled antibodies against one or more of the cell surface markers expressed by the MDCs (C. Webster et al., 1988, Exp. Cell. Res. 174:252 65; J. R. Blanton et al., 1999, Muscle Nerve 22:43 50). For example, FACS analysis can be performed using labeled antibodies that specifically bind to CD34, Flk-1, Sca-1, and/or the other cell-surface markers described herein to select a population of PP6-like cells that exhibit long-term survivability when introduced into the host tissue. Also encompassed by the present invention is the use of one or more fluorescence-detection labels, for example, fluorescein or rhodamine, for antibody detection of different cell marker proteins.

Using any of the MDCs isolation methods described above, MDCs that are to be transported, or are not going to be used for a period of time may be preserved using methods known in the art. More specifically, the isolated MDCs may be frozen to a temperature ranging from about −25 to about −90° C. Preferably, the MDCs are frozen at about −80° C., on dry ice for delayed use or transport. The freezing may be done with any cryopreservation medium known in the art.

Muscle-Derived Cell-Based Treatments

In one embodiment of the present invention, the MDCs are isolated from a skeletal muscle source and introduced or transplanted into a muscle or non-muscle soft tissue site of interest, or into bone structures. Advantageously, the MDCs of the present invention are isolated and enriched to contain a large number of progenitor cells showing long-term survival following transplantation. In addition, the muscle-derived progenitor cells of this invention express a number of characteristic cell markers, such desmin, CD34, and Bc1-2. Furthermore, the muscle-derived progenitor cells of this invention express the Sca-1, and Flk-1 cell markers, but do not express the CD45 or c-Kit cell markers (see Example 1).

MDCs and compositions comprising MDCs of the present invention can be used to repair, treat, or ameliorate various aesthetic or functional conditions (e.g. defects) through the augmentation of bone. In particular, such compositions can be used for the treatment of bone disorders. Multiple and successive administrations of MDC are also embraced by the present invention.

For MDC-based treatments, a skeletal muscle explant is preferably obtained from an autologous or heterologous human or animal source. An autologous animal or human source is more preferred. MDC compositions are then prepared and isolated as described herein. To introduce or transplant the MDCs and/or compositions comprising the MDCs according to the present invention into a human or animal recipient, a suspension of mononucleated muscle cells is prepared. Such suspensions contain concentrations of the muscle-derived progenitor cells of the invention in a physiologically-acceptable carrier, excipient, or diluent. For example, suspensions of MDC for administering to a subject can comprise $10^8$ to $10^9$ cells/ml in a sterile solution of complete medium modified to contain the subject's serum, as an alternative to fetal bovine serum. Alternatively, MDC suspensions can be in serum-free, sterile solutions, such as cryopreservation solutions (Celox Laboratories, St. Paul, Minn.). The MDC suspensions can then be introduced e.g., via injection, into one or more sites of the donor tissue.

In certain embodiments, the described cells are administered as a pharmaceutically or physiologically acceptable preparation or composition containing a physiologically acceptable carrier, excipient, or diluent, and administered to the tissues of the recipient organism of interest, including humans and non-human animals. In other embodiments, the MDC-containing composition are prepared by resuspending the cells in a suitable liquid or solution such as sterile physiological saline or other physiologically acceptable injectable aqueous liquids. The amounts of the components to be used in such compositions can be routinely determined by those having skill in the art.

According to the invention, the MDCs or compositions thereof can be administered by placement of the MDC suspensions onto a biocompatible matrix, e.g., small intestine submucosa (SIS). In some embodiments, the MDCs are inserted into the biocompatible matrix and then the MDC-containing matrix into or onto the site of interest. Alternatively, the MDCs can be administered by parenteral routes of injection, including subcutaneous, intravenous, intramuscular, and intrasternal to the desired tissue that has already been administered the biocompatible material.

To optimize transplant success, the closest possible immunological match between donor and recipient is desired. If an autologous source is not available, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the transplant procedure. For example, cyclosporin A or other immunosuppressive drugs can be administered to the transplant recipient. Immunological tolerance may also be induced prior to transplantation by alternative methods known in the art (D. J. Watt et al., 1984, Clin. Exp. Immunol. 55:419; D. Faustman et al., 1991, Science 252:1701).

Consistent with the present invention, the MDCs can be administered to body tissues, including bone in the presence of a biocompatible matrix. The number of cells in an MDC suspension and the mode of administration may vary depending on the site and condition being treated. From about $1.0 \times 10^5$ to about $1 \times 10^8$ MDCs may be administered according to the invention. As a non-limiting example, in accordance with the present invention, about $0.5-3.0 \times 10^6$ MDCs. Preferably $2.0 \times 10^6$ MDCs are administered in combination with a biocompatible matrix.

For bone augmentation or treatment of bone disorders, the MDCs are prepared as described above and are administered, e.g. in combination with a biocompatible matrix at the site of treatment or via injection, onto, into or around bone tissue pretreated with the biocompatible matrix to provide additional bone density and/or volume. As is appreciated by the skilled practitioner, the number of MDC introduced is modulated to provide varying amounts of bone density and/or bone volume, as needed or required. In certain embodiments, about $1.0-3.0 \times 10^6$ MDCs are injected for the augmentation of bone in combination with a biocompatible matrix. Thus, the present invention also embraces the use of MDC of the invention in treating bone disorders or enhancing bone density and/or bone volume. Bone disorders include osteoporosis, Paget's Disease, osteogenesis imperfecta, bone fracture, osteomalacia, decrease in bone trabecular strength, decrease in bone cortical strength and decrease in bone density with old age. The invention also relates to the novel use of MDCs for the increase of bone mass in athletes or other organisms in need of greater than average bone mass.

Biocompatible Matrices

According to some embodiments of the present invention, MDCs are mixed with the biocompatible matrix material in vitro not long before application to a tissue or organ site in vivo. Alternatively, MDCs can be mixed with, or inoculated onto, the biocompatible matrix material just at the time of use. In some cases, depending upon cell source, cell concentration and matrix material, the admixing of MDCs and biocompatible matrix material, or the inoculation of stem cells onto matrix material, needs no more time than the time that it takes to combine the MDCs and the biocompatible matrix at the point of use.

In accordance with the present invention, the in vitro incubation of MDCs with biocompatible matrix material is performed for from about 5 seconds to less than about 12 hours, preferably for from about 5 seconds to about 30 minutes. The in vitro incubation of MDCs with matrix material according to this invention is generally less than about 3 hours, preferably, less than about 1 hour, more preferably, less than about 30 minutes. In some embodiments of the invention, long-term (e.g., >about 12 hours, days, or weeks) of incubation or culture time is necessary to achieve results using the combination of MDC-biocompatible matrix material.

The compositions of the invention can be used in treatments for bone disorders include osteoporosis, Paget's Disease, osteogenesis imperfecta, bone fracture, osteomalacia, decrease in bone trabecular strength, decrease in bone cortical strength and decrease in bone density with old age.

A variety of biological or synthetic solid matrix materials (i.e., solid support matrices, biological adhesives or dressings, and biological/medical scaffolds) are suitable for use as the biocompatible matrix of the invention. The biocompatible matrix material is preferably medically acceptable for use in in vivo applications. Nonlimiting examples of such medically acceptable and/or biologically or physiologically acceptable or compatible materials include, but are not limited to, solid matrix materials that are absorbable and/or non-absorbable, such as small intestine submucosa (SIS), e.g., porcine-derived (and other SIS sources); crosslinked or non-crosslinked alginate, hydrocolloid, foams, collagen gel, collagen sponge, polyglycolic acid (PGA) mesh, polyglactin (PGL) mesh, fleeces, foam dressing, bioadhesives (e.g., fibrin glue and fibrin gel) and dead de-epidermized skin equivalents in one or more layers. As an exemplary bioadhesive, fibrin glue preparations have been described in WO 93/05067 to Baxter International, Inc., WO 92/13495 to Fibratek, Inc. WO 91/09641 to Cryolife, Inc., and U.S. Pat. Nos. 5,607,694 and 5,631,019 to G. Marx. Preferably, the biocompatible matrix material is SIS.

In an embodiment of the present invention, the biocompatible matrix material can be in the form of a sling, patch, wrap, such as are employed in surgeries to correct, strengthen, or otherwise repair tissues in need of such treatment.

In another embodiment, the biocompatible matrix, either combined with MDCs or alone, can be applied through a minimally invasive fiberoptic scope (e.g., laparoscope) to bone. In another embodiment, the biocompatible matrix, either combined with MDCs or alone, is applied via orthopedic endoscopy to coat the outside of damaged or weakened bone or disc to promote and/or improve healing and strength, and/or to prevent degeneration.

Genetically Engineered Muscle-Derived Cells

In another aspect of the present invention, the MDCs of this invention may be genetically engineered to contain a nucleic acid sequence(s) encoding one or more active biomolecules, and to express these biomolecules, including proteins, polypeptides, peptides, hormones, metabolites, drugs, enzymes, and the like. Such MDCs may be histocompatible (autologous) or nonhistocompatible (allogeneic) to the recipient, including humans. These cells can serve as long-term local delivery systems for a variety of treatments, for example, for the treatment of bone diseases and pathologies, including, but not limited to osteoporosis, Paget's Disease, osteogenesis imperfecta, bone fracture, osteomalacia, decrease in bone trabecular strength, decrease in bone cortical strength and decrease in bone density with old age.

Preferred in the present invention are autologous muscle-derived progenitor cells, which will not be recognized as foreign to the recipient. In this regard, the MDC used for cell-mediated gene transfer or delivery will desirably be matched vis-a-vis the major histocompatibility locus (MHC or HLA in humans). Such MHC or HLA matched cells may be autologous. Alternatively, the cells may be from a person having the same or a similar MHC or HLA antigen profile. The patient may also be tolerized to the allogeneic MHC antigens. The present invention also encompasses the use of cells lacking MHC Class I and/or II antigens, such as described in U.S. Pat. No. 5,538,722, incorporated herein by reference.

The MDCs may be genetically engineered by a variety of molecular techniques and methods known to those having skill in the art, for example, transfection, infection, or transduction. Transduction as used herein commonly refers to cells that have been genetically engineered to contain a foreign or heterologous gene via the introduction of a viral or non-viral vector into the cells. Transfection more commonly refers to cells that have been genetically engineered to contain a foreign gene harbored in a plasmid, or non-viral vector. MDCs can be transfected or transduced by different vectors and thus can serve as gene delivery vehicles to transfer the expressed products into muscle.

Although viral vectors are preferred, those having skill in the art will appreciate that the genetic engineering of cells to contain nucleic acid sequences encoding desired proteins or polypeptides, cytokines, and the like, may be carried out by methods known in the art, for example, as described in U.S. Pat. No. 5,538,722, including fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, and the like.

Vectors for introducing heterologous (i.e., foreign) nucleic acid (DNA or RNA) into muscle cells for the expression of bioactive products are well known in the art. Such vectors possess a promoter sequence, preferably, a promoter that is cell-specific and placed upstream of the sequence to be expressed. The vectors may also contain, optionally, one or more expressible marker genes for expression as an indication of successful transfection and expression of the nucleic acid sequences contained in the vector.

Illustrative examples of vehicles or vector constructs for transfection or infection of the muscle-derived cells of the present invention include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. Examples of such functional sequences include polynucleotide, e.g., DNA or RNA, sequences comprising transcriptional and translational initiation and termination regulatory sequences, including promoters (e.g., strong promoters, inducible promoters, and the like) and enhancers which are active in muscle cells.

Also included as part of the functional sequences is an open reading frame (polynucleotide sequence) encoding a protein of interest; flanking sequences may also be included for site-directed integration. In some situations, the 5'-flanking sequence will allow homologous recombination, thus changing the nature of the transcriptional initiation region, so as to provide for inducible or noninducible transcription to increase or decrease the level of transcription, as an example.

In general, the nucleic acid sequence desired to be expressed by the muscle-derived progenitor cell is that of a structural gene, or a functional fragment, segment or portion of the gene, that is heterologous to the muscle-derived progenitor cell and encodes a desired protein or polypeptide product, for example. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. Examples of genes of interest for use in accordance with the present invention include genes encoding cell growth factors, cell differentiation factors, cell signaling factors and programmed cell death factors. Specific examples include, but are not limited to, genes encoding BMP-2 (rhBMP-2), IL-1Ra, Factor IX, and connexin 43.

As mentioned above, a marker may be present for selection of cells containing the vector construct. The marker may be an inducible or non-inducible gene and will generally allow for positive selection under induction, or without induction, respectively. Examples of commonly-used marker genes include neomycin, dihydrofolate reductase, glutamine synthetase, and the like.

The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the muscle-derived cells. Such replication systems are represented by replication-defective adenovirus constructed as described, for example, by G. Acsadi et al., 1994, Hum. Mol. Genet. 3:579 584, and by Epstein-Ban virus. Examples of replication defective vectors, particularly, retroviral vectors that are replication defective, are BAG, described by Price et al., 1987, Proc. Natl. Acad. Sci. USA, 84:156; and Sanes et al., 1986, EMBO J., 5:3133. It will be understood that the final gene construct may contain one or more genes of interest, for example, a gene encoding a bioactive metabolic molecule. In addition, cDNA, synthetically produced DNA or chromosomal DNA may be employed utilizing methods and protocols known and practiced by those having skill in the art.

If desired, infectious replication-defective viral vectors may be used to genetically engineer the cells prior to in vivo injection of the cells. In this regard, the vectors may be introduced into retroviral producer cells for amphotrophic packaging. The natural expansion of muscle-derived progenitor cells into adjacent regions obviates a large number of injections into or at the site(s) of interest.

In another aspect, the present invention provides ex vivo gene delivery to cells and tissues of a recipient mammalian host, including humans, through the use of MDC, e.g., early progenitor muscle cells, that have been virally transduced using an adenoviral vector engineered to contain a heterologous gene encoding a desired gene product. Such an ex vivo approach provides the advantage of efficient viral gene transfer, which is superior to direct gene transfer approaches. The ex vivo procedure involves the use of the muscle-derived progenitor cells from isolated cells of muscle tissue. The muscle biopsy that will serve as the source of muscle-derived progenitor cells can be obtained from an injury site or from another area that may be more easily obtainable from the clinical surgeon.

It will be appreciated that in accordance with the present invention, clonal isolates can be derived from the population of muscle-derived progenitor cells (i.e., PP6 cells or "slowly adhering" cells using the single plate procedure) using various procedures known in the art, for example, limiting dilution plating in tissue culture medium. Clonal isolates comprise genetically identical cells that originate from a single, solitary cell. In addition, clonal isolates can be derived using FACS analysis as described above, followed by limiting dilution to achieve a single cell per well to establish a clonally isolated cell line. An example of a clonal isolate derived from the PP6 cell population is mc13, which is described in Example 1. Preferably, MDC clonal isolates are utilized in the present methods, as well as for genetic engineering for the expression of one or more bioactive molecules, or in gene replacement therapies.

The MDCs are first infected with engineered viral vectors containing at least one heterologous gene encoding a desired gene product, suspended in a physiologically acceptable carrier or excipient, such as saline or phosphate buffered saline, and then administered to an appropriate site in the host. Consistent with the present invention, the MDCs can be administered to body tissues, including bone, as described above. The desired gene product is expressed by the injected cells, which thus introduce the gene product into the host. The introduced and expressed gene products can thereby be utilized to treat, repair, or ameliorate the injury, dysfunction, or disease, due to their being expressed over long time periods by the MDCs of the invention, having long-term survival in the host.

In animal model studies of myoblast-mediated gene therapy, implantation of $10^6$ myoblasts per 100 mg muscle was required for partial correction of muscle enzyme defects (see, J. E. Morgan et al., 1988, J. Neural. Sci. 86:137; T. A. Partridge et al., 1989, Nature 337:176). Extrapolating from this data, approximately $10^{12}$ MDCs suspended in a physiologically compatible medium can be implanted into muscle tissue for gene therapy for a 70 kg human. This number of MDC of the invention can be produced from a single 100 mg skeletal muscle biopsy from a human source (see below). For the treatment of a specific injury site, an injection of genetically engineered MDC into a given tissue or site of injury comprises a therapeutically effective amount of cells in solution or suspension, preferably, about $10^5$ to $10^6$ cells per cm$^3$ of tissue to be treated, in a physiologically acceptable medium.

EXAMPLES

Example 1

MDC Enrichment, Isolation and Analysis According to the Pre-Plating Method

MDCs were prepared as described (U.S. Pat. No. 6,866,842 of Chancellor et al.). Muscle explants were obtained from the hind limbs of a number of sources, namely from 3-week-old mdx (dystrophic) mice (C57BL/10ScSn mdx/mdx, Jackson Laboratories), 4-6 week-old normal female SD (Sprague Dawley) rats, or SCID (severe combined immunodeficiency) mice. The muscle tissue from each of the animal sources was dissected to remove any bones and minced into a slurry. The slurry was then digested by 1 hour serial incubations with 0.2% type XI collagenase, dispase (grade II, 240 unit), and 0.1% trypsin at 37° C. The resulting cell suspension was passed through 18, 20, and 22 gauge needles and centrifuged at 3000 rpm for 5 minutes. Subsequently, cells were suspended in growth medium (DMEM supplemented with 10% fetal bovine serum, 10% horse serum, 0.5% chick embryo extract, and 2% penicillin/streptomycin). Cells were then preplated in collagen-coated flasks (U.S. Pat. No. 6,866,842 of Chancellor et al.). After approximately 1 hour, the supernatant was removed from the flask and re-plated into a fresh collagen-coated flask. The cells which adhered rapidly within this 1 hour incubation were mostly fibroblasts (Z. Qu et al., supra; U.S. Pat. No. 6,866,842 of Chancellor et al.). The supernatant was removed and re-plated after 30-40% of the cells had adhered to each flask. After approximately 5-6 serial platings, the culture was enriched with small, round cells, designated as PP6 cells, which were isolated from the starting cell population and used in further studies. The adherent cells isolated in the early platings were pooled together and designated as PP1-4 cells.

The mdx PP1-4, mdx PP6, normal PP6, and fibroblast cell populations were examined by immunohistochemical analysis for the expression of cell markers. The results of this analysis are shown in Table 1.

TABLE 1

Cell markers expressed in PP1-4 and PP6 cell populations.

| | mdx PP1-4 cells | mdx PP6 cells | nor PP6 cells | fibroblasts |
|---|---|---|---|---|
| desmin | +/− | + | + | − |
| CD34 | − | + | + | − |
| Bcl-2 | (−) | + | + | − |
| Flk-1 | na | + | + | − |
| Sca-1 | na | + | + | − |
| M-cadherin | −/+ | −/+ | −/+ | − |
| MyoD | −/+ | +/− | +/− | − |
| myogenin | −/+ | +/− | +/− | − |

Mdx PP1-4, mdx PP6, normal PP6, and fibroblast cells were derived by preplating technique and examined by immunohistochemical analysis. "−" indicates less than 2% of the cells showed expression; "(−)"; "−/+" indicates 5-50% of the cells showed expression; "+/−" indicates ~40-80% of the cells showed expression; "+" indicates that >95% of the cells showed expression; "nor" indicates normal cells; "na" indicates that the immunohistochemical data is not available.

It is noted that both mdx and normal mice showed identical distribution of all the cell markers tested in this assay. Thus, the presence of the mdx mutation does not affect the cell marker expression of the isolated PP6 muscle-cell derived population.

MDCs were grown in proliferation medium containing DMEM (Dulbecco's Modified Eagle Medium) with 10% FBS (fetal bovine serum), 10% HS (horse serum), 0.5% chick embryo extract, and 1% penicillin/streptomycin, or fusion medium containing DMEM supplemented with 2% fetal bovine serum and 1% antibiotic solution. All media supplies were purchased through Gibco Laboratories (Grand Island, N.Y.).

Example 2

MDC Enrichment, Isolation and Analysis According to the Single Plate Method

Populations of rapidly- and slowly-adhering MDCs were isolated from skeletal muscle of a mammalian subject. The subject may be a human, rat, dog or other mammal. Biopsy size ranged from 42 to 247 mg.

Skeletal muscle biopsy tissue is immediately placed in cold hypothermic medium (HYPOTHERMOSOL® (BioLife) supplemented with gentamicin sulfate (100 ng/ml, Roche)) and stored at 4° C. After 3 to 7 days, biopsy tissue is removed from storage and production is initiated. Any connective or non-muscle tissue is dissected from the biopsy sample. The remaining muscle tissue that is used for isolation is weighed. The tissue is minced in Hank's Balanced Salt Solution (HBSS), transferred to a conical tube, and centrifuged (2,500×g, 5 minutes). The pellet is then resuspended in a Digestion Enzyme solution (Liberase Blendzyme 4 (0.4-1.0 U/mL, Roche)). 2 mL of Digestion Enzyme solution is used per 100 mg of biopsy tissue and is incubated for 30 minutes at 37° C. on a rotating plate. The sample is then centrifuged (2,500×g, 5 minutes). The pellet is resuspended in culture medium and passed through a 70 µm cell strainer. The culture media used for the procedures described in this Example was Cambrex Endothelial Growth Medium EGM-2 basal medium supplemented with the following components: i. 10% (v/v) fetal bovine serum, and ii. Cambrex EGM-2 SingleQuot Kit, which contains: Insulin Growth Factor-1 (IGF-1), Basic Fibroblast Growth Factor (bFGF), Vascular Endothelial Growth Factor (VEGF), Epidermal Growth Factor (EGF), Hydrocortisone, Heparin, and Ascorbic Acid. The filtered cell solution is then transferred to a T25 culture flask and incubated for 30-120 minutes at 37° C. in 5% $CO_2$. Cells that attach to this flask are the "rapidly-adhering cells".

After incubation, the cell culture supernatant is removed from the T25 flask and placed into a 15 mL conical tube. The T25 culture flask is rinsed with 2 mL of warmed culture medium and transferred to the aforementioned 15 mL conical tube. The 15 mL conical tube is centrifuged (2,500×g, 5 minutes). The pellet is resuspended in culture medium and transferred to a new T25 culture flask. The flask is incubated for ~2 days at 37° C. in 5% CO2 (cells that attach to this flask are the "slowly-adhering cells"). After incubation, the cell culture supernatant is aspirated and new culture medium is added to the flask. The flask is then returned to the incubator for expansion. Standard culture passaging is carried out from here on to maintain the cell confluency in the culture flask at less than 50%. Trypsin-EDTA (0.25%, Invitrogen) is used to detach the adherent cells from the flask during passage. Typical expansion of the "slowly-adhering cells" takes an average of 17 days (starting from the day production is initiated) to achieve an average total viable cell number of 37 million cells.

Once the desired cell number is achieved, the cells are harvested from the flask using Trypsin-EDTA and centrifuged (2,500×g, 5 minutes). The pellet is resuspended in BSS-P solution (HBSS supplemented with human serum albumin (2% v/v, Sera Care Life)) and counted. The cell solution is then centrifuged again (2,500×g, 5 minutes), resuspended with Cryopreservation Medium (CryoStor (Biolife) supplemented with human serum albumin (2% v/v, Sera Care Life Sciences)) to the desired cell concentration, and packaged in the appropriate vial for cryogenic storage. The cryovial is placed into a freezing container and placed in the −80° C. freezer. Cells are administered by thawing the frozen cell suspension at room temperature with an equal volume of physiologic saline and injected directly (without additional manipulation). The lineage characterization of the slowly adhering cell populations shows: Myogenic (87.4% CD56+, 89.2% desmin+), Endothelial (0.0% CD31+), Hematopoietic (0.3% CD45+), and Fibroblast (6.8% CD90+/CD56−).

Following disassociation of the skeletal muscle biopsy tissue, two fractions of cells were collected based on their rapid or slow adhesion to the culture flasks. The cells were then expanded in culture with growth medium and then frozen in cryopreservation medium ($3\times10^5$ cells in 15 µl) in a 1.5 ml eppendorf tube. For the control group, 15 µl of cryopreservation medium alone was placed into the tube. These tubes were stored at −80° C. until injection. Immediately prior to injection, a tube was removed from storage, thawed at room temperature, and resuspended with 15 µl of 0.9% sodium chloride solution.

Cell count and viability was measured using a Guava flow cytometer and Viacount assay kit (Guava). CD56 was measured by flow cytometry (Guava) using PE-conjugated anti-CD56 antibody (1:50, BD Pharmingen) and PE-conjugated isotype control monoclonal antibody (1:50, BD Pharmingen). Desmin was measured by flow cytometry (Guava) on paraformaldehyde-fixed cells (BD Pharmingen) using a monoclonal desmin antibody (1:100, Dako) and an isotype control monoclonal antibody (1:200, BD Pharmingen). Fluorescent labeling was performed using a Cy3-conjugated anti-mouse IgG antibody (1:250, Sigma). In between steps, the cells were washed with permeabilization buffer (BD Pharmingen). For creatine kinase (CK) assay, $1\times10^5$ cells were plated per well into a 12 well plate in differentiation-inducing medium. Four to 6 days later, the cells were harvested by trypsinization and centrifuged into a pellet. The cell lysis supernatant was assayed for CK activity using the CK Liqui-UV kit (Stanbio).

Example 3

Small Intestine Submucosa Alleviates the Repair of a Critical Size Calvarial Defect in Mice The purpose of this study was to investigate the bone regenerative potential of single-layer SIS scaffold transplanted into critical size calvarial defect in mice. We also preconditioned SIS grafts by seeding them with human muscle-derived cells (hMDCs), prepared as detailed in Example 2, above, in order to test osteogenic potential of this construct in response to natural fracture environment.

Materials and Methods

In this study a total of 24 SCID mice were used. All animal experiments were approved by institutional ARCC. Surgical procedure was performed under general anesthesia. Critical size calvarial bone defect was created using a 5-mm-diameter trephine burr. Human muscle-derived cells (hMDCs) isolated from a 35 year old male patient were provided. Animals were divided into 3 groups according to the treatment they received. A control group consisted of untreated mice with a calvarial defect void of cells or SIS. The second group consisted of mice receiving 5×5 mm single layer of SIS sheet (Cook Biotech, Inc) without cells that was placed on top of the defect. The third group consisted of mice receiving 5×5 mm single layer SIS sheet that was seeded with $2\times10^6$ human muscle-derived cells hMDCs twelve hours before transplantation. Microcomputed tomography (vivaCT40, Scanco) of the calvaria was performed on the following day after the surgery for each animal. Four animals in each group were sacrificed at 4 and 10 weeks and harvested calvaria were evaluated by microCT for a new bone formation. Specimens were fixed in 10% neutral buffered formalin and preserved for later histological analysis.

Figure 2:
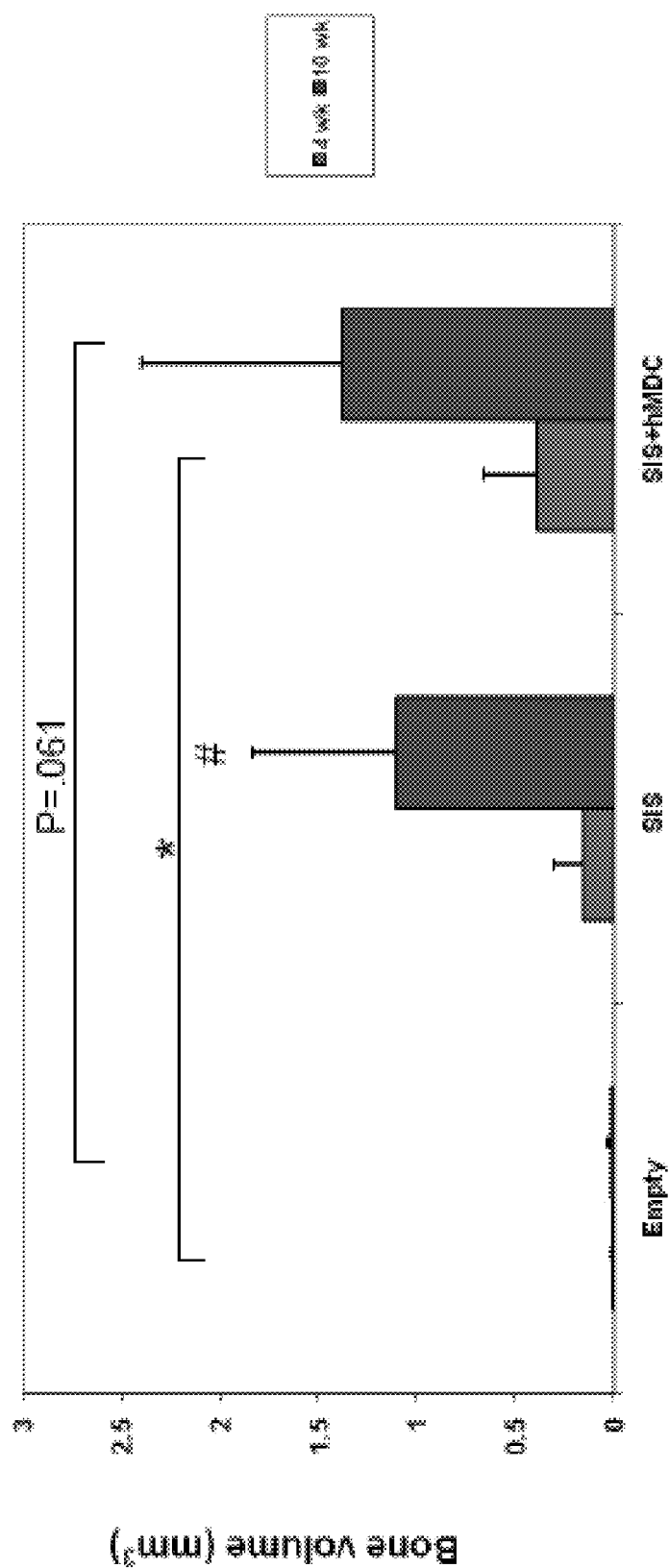
FIG. 2 is a bar graph showing new bone formation in calvarial defects at 4 and 10 weeks.
Figure 3:
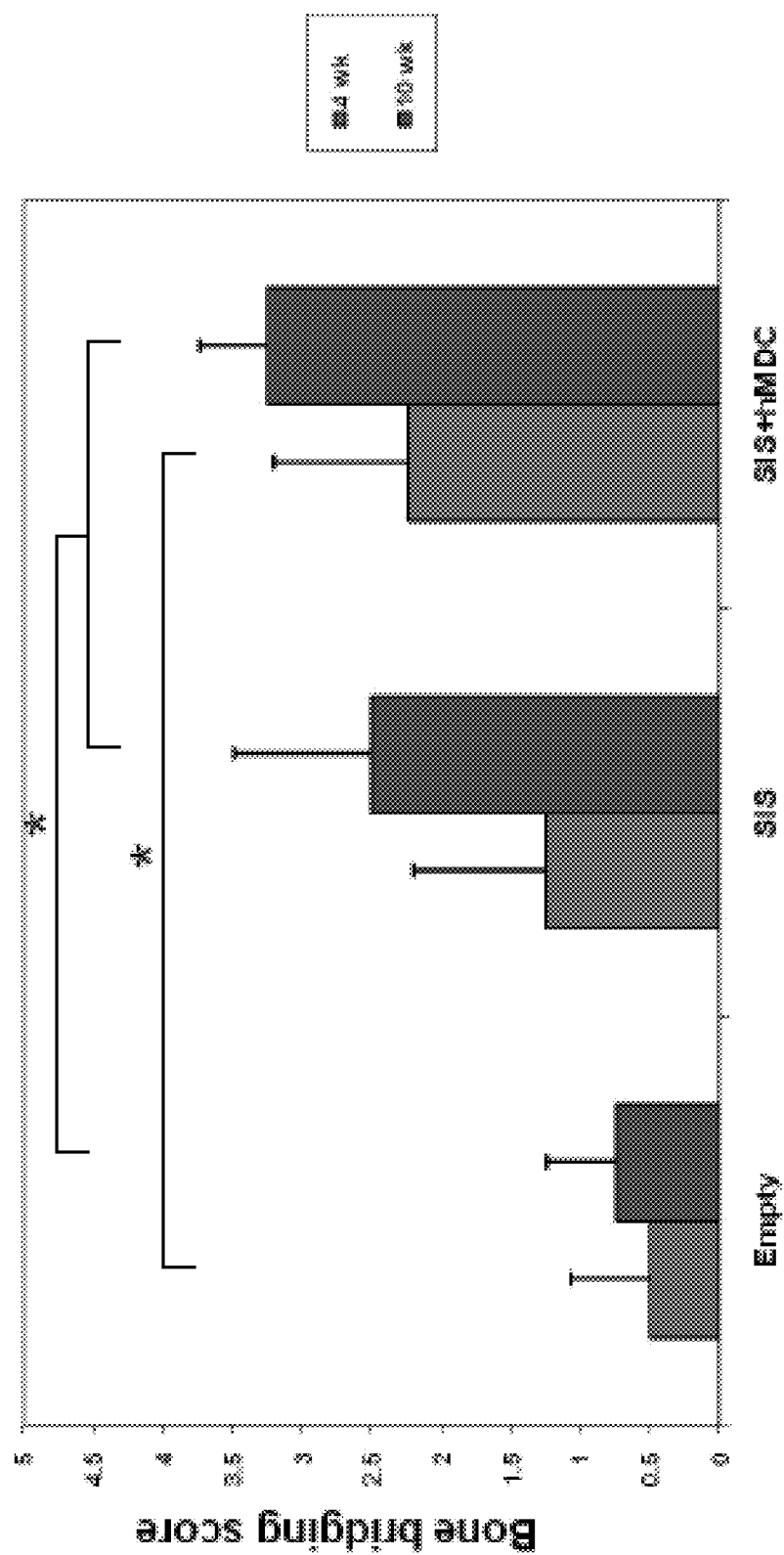
FIG. 3 is a bar graph showing a bone bridging score for mice treated with SIS with and without MDCs at 4 and 10 weeks.

Results 3D reconstruction of the untreated calvaria did not revealed any substantial bone formation within the defects at 4 and 10 weeks (FIGS. 1A and 1D). Bone regeneration was seen only along the rim of the defect which remained entirely open and did not contain any islands of new bone. At 4 weeks the calvarial defects that were treated with SIS sheet without cells contained very small or undetectable bone formation mostly along the edge of the defect (FIG. 1B). At the same time defects treated with SIS sheet seeded with hMDCs contained obvious islands of newly formed bone (FIG. 1C). At 10 weeks we detected large islands of new bone in both SIS, and SIS-hMDC-treated calvarial defects (FIGS. 1E and 1F). Quantification of new bone within volume of interest (VOI) using Scanco imaging software revealed difference between control-untreated and SIS-treated defects at 4 and 10 weeks (FIG. 2). At 4 weeks the new bone volume was $0.01\pm0.005$ mm$^3$ in the control group, $0.16\pm0.15$ mm$^3$ in the SIS-treated group, and $0.4\pm0.27$ mm$^3$ in the SIS-hMDC-treated group. At 10 weeks the new bone volume increased up to $0.02\pm0.02$ mm$^3$ in the control group, $1.11\pm0.73$ mm$^3$ in the SIS-treated group, and $1.38\pm1.02$ mm$^3$ in the SIS-hMDC-treated group. The SIS-hMDC treatment group had significantly more bone at 4 and 10 weeks compared to the empty (untreated) group. Also, there was significant increase in bone volume in the SIS-treated group at 10 weeks compared to the 4 week time point. FIG. 3 contains important information and supports our previous results showing significant difference in bony bridging score between the SIS-hMDC-treated group and the empty group at 4 and 10 weeks. (Patel et al. Bone, 43:931-940 (2008), provides methods for determining a bony bridging score and is incorporated herein by reference in its entirety). The data suggests that the combination of MDCs with SIS administered to subjects leads to faster healing of bone.

Discussion

This study demonstrated that SIS grafts function as a regenerative matrix scaffold, guiding the attachment of host cells and supporting formation of new bone. Enhanced bone formation was observed in SIS-treated calvarial defects in mice, while control untreated defects showed only minimal calcification Bone formation in SIS-treated calvarias was already visible after 4 weeks and gradually increased over 10 week period. Addition of human muscle-derived cells to the SIS grafts apparently enhanced calvarial defect healing.

Example 4 hMDCs Seeded on SIS Undergo Osteogenesis In Vitro

Methods:

$2\times10^6$ human muscle-derived cells were seeded on pre-cut 6 mm diameter 4 layer SIS disks and incubated for 28 days in either proliferation medium (n=3) containing phenol red-free Dulbecco's Modified Eagle's Medium (DMEM) (Invitrogen) supplemented with 110 mg/L sodium pyruvate (Sigma-Aldrich), 584 mg/L L-Glutamine, 10% fetal bovine serum (FBS), 10% horse serum (HS), 1% penicillin/streptomycin (all from Invitrogen), and 0.5% chick embryo extract (Accurate Chemical Co.), or osteogenic medium (n=6) containing phenol-red free DMEM, 10% FBS, 1% Penicillin/streptomycin, 10-7 M dexamethasone, $5\times10^{-5}$ M ascorbic-acid-2-phosphate, $10^{-2}$ M β-glycerophosphate]. at 36° C. in the presence of 5% $CO_2$ with medium change every 2-3 days. SIS scaffolds without cells were used for the control and cultivated similarly in either osteogenic (n=6) or proliferation (n=4) medium. The same human cells were used to make four cell pellets (250,000 cells/pellet) that were incubated for 28 days in osteogenic medium. All scaffolds and cell pellets undergo micro-CT scanning at 7, 10, 14, 21, and 28 days and were evaluated for mineralized matrix volume and density.

Figure 4A:
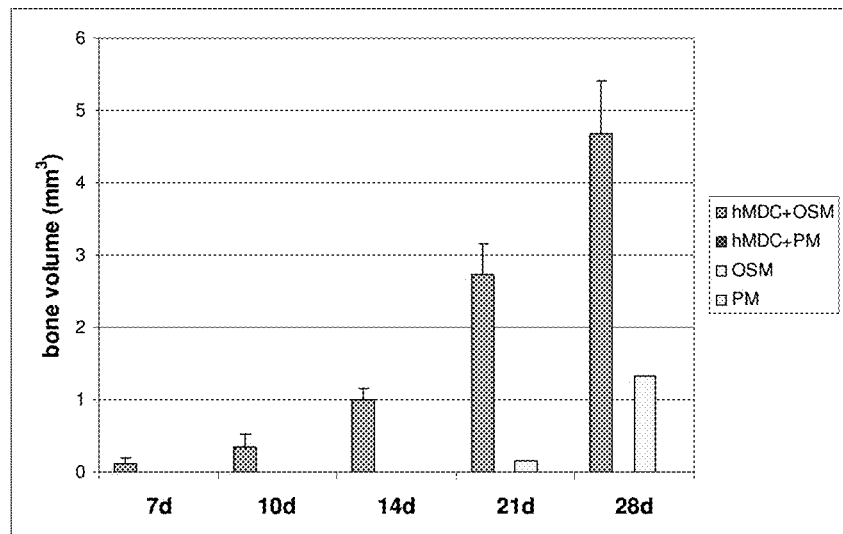
FIG. 4A is a bar graph showing the volume of bone matrix formation on SIS with and without hMDCs and with osteogenic or proliferation medium (OSM and PM, respectively) at 7, 10, 14, 21 and 28 days.
Figure 4B:
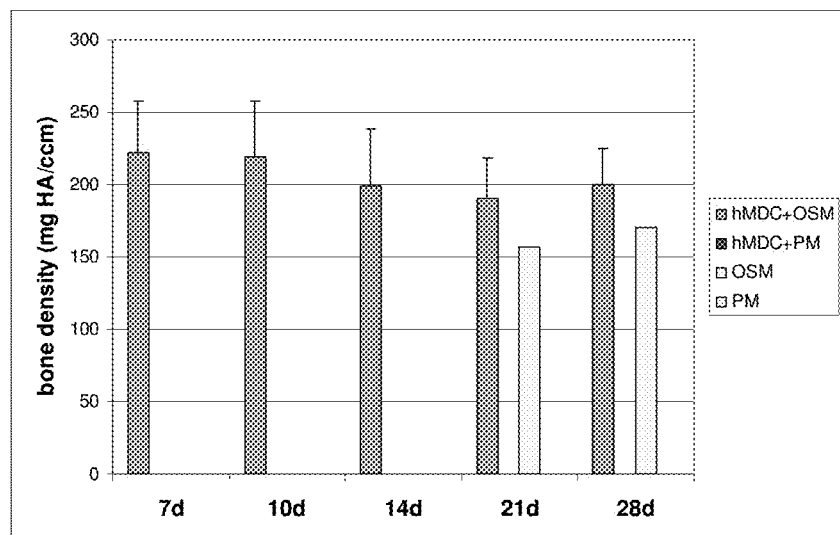
FIG. 4B is a bar graph showing the density of bone matrix formation on SIS with and without hMDCs and with OSM or PM at 7, 10, 14, 21 and 28 days.
Figure 5:
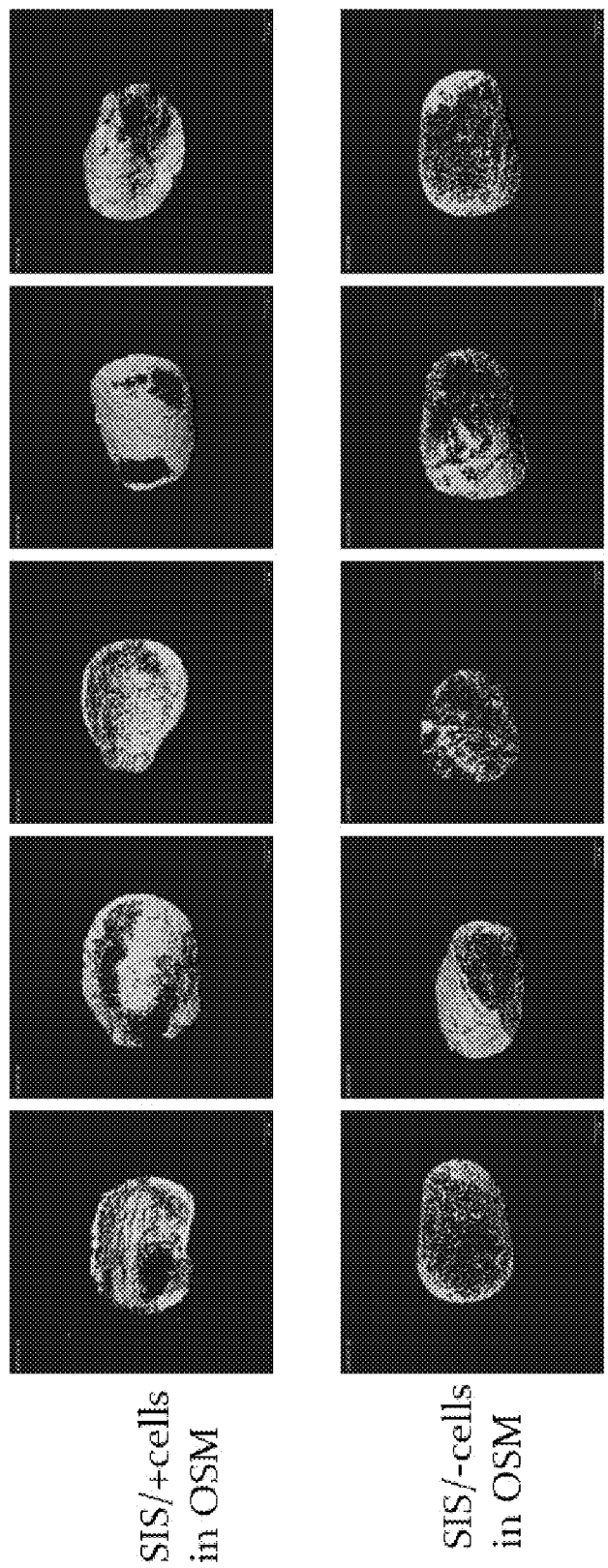
FIG. 5 is a 3D reconstruction of the SIS with and without hMDCs and with OSM or PM at 28 days.

Results:

3D reconstruction by micro-CT revealed presence of mineralization as early as 7 days in human cell-populated SIS scaffolds cultured in osteogenic medium. The mineralized matrix volume in this group progressively increased from $0.112\pm0.09$ mm$^3$, as observed at 7 days, to $4.673\pm0.72$ mm$^3$, as detected at 28 days (FIG. 4A). No matrix mineralization during the entire culture period was detected in SIS scaffolds containing human cells that were placed in proliferation medium. Empty SIS scaffolds containing no cells also exhibited mineral deposition at 21 days ($0.162\pm0.19$ mm$^3$) and 28 days ($1.329\pm0.8$ mm$^3$) when cultured in osteogenic medium, but did not conduce to mineralization when cultivated in proliferation medium. The mineralized matrix density in SIS scaffolds with human cells cultivated in osteogenic medium was $222.31\pm35.7$ mm HA/ccm at 7 days, and slightly decreased to $200.05\pm25.4$ mm HA/ccm at 28 days (FIG. 4B). Density of empty SIS scaffolds cultured in OSM was $157.09\pm7.2$ mm HA/ccm at 21 day and $170.05\pm20.12$ mm HA/ccm at 728 days (FIG. 4B). FIG. 5 shows 3D micro-CT reconstruction of SIS and SIS-hMDC scaffolds (5 samples in each group) cultured in osteogenic medium on day 28. It demonstrates that hMDC-seeded SIS scaffolds have more intense mineralization than SIS scaffolds without cells suggesting that hMDCs accelerated the formation of mineralized matrix on SIS sheets.

Figure 6A:
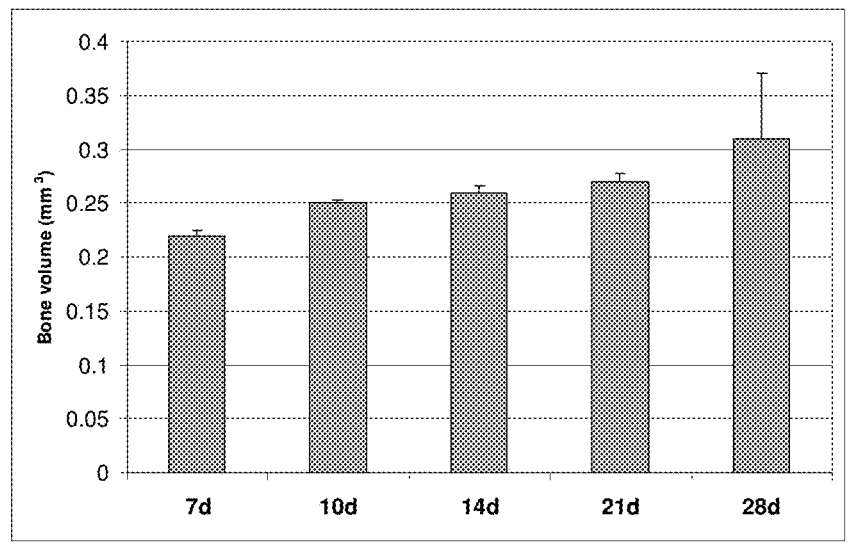
FIG. 6A is a bar graph showing the volume of bone matrix formation on cell pellets at 7, 10, 14, 21 and 28 days.
Figure 6B:
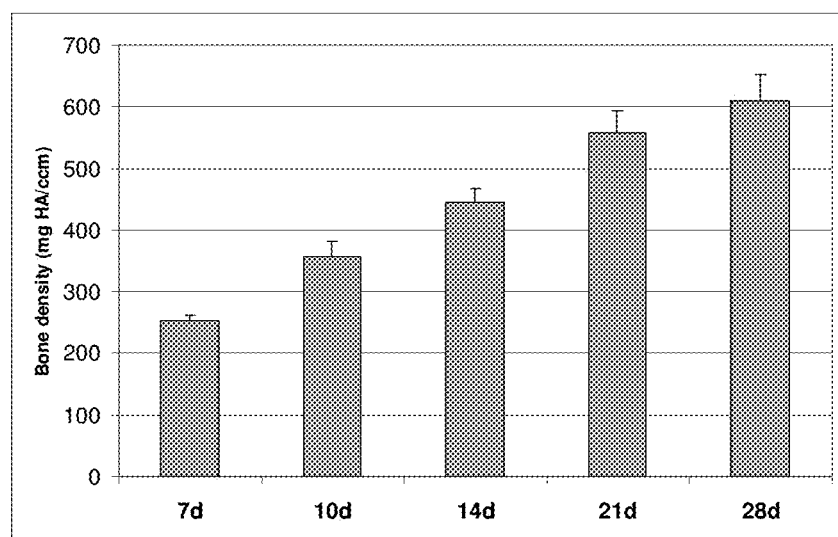
FIG. 6B is a bar graph showing the density of bone matrix formation on cell pellets at 7, 10, 14, 21 and 28 days.

Micro-CT scanning of human cell pellets cultured in osteogenic medium revealed matrix mineralization to a lesser extent. The initial matrix volume detected at 7 days ($0.221\pm0.004$ mm$^3$) was merely increased at 28 days ($0.31\pm0.06$ mm$^3$) (FIG. 6A). However, mineralized matrix density in pellet cultures increased noticeably. It was $252.2\pm9.96$ mg HA/ccm at 7 days, $445.34\pm22.55$ mg HA/ccm at 14 days, and $609.01\pm42.82$ mm HA/ccm at 28 days (FIG. 6B).

We do not wish to be limited by theory, however, the effect of increased volume produced when using SIS and increased density when using pellets could be caused by the difference of the cells being spread out on SIS as opposed to compacted into a tight pellet. The cells on SIS are spread out and are simply creating bone over the entire SIS area. Thus, the effect seen is increased bone volume during the period of evaluation. Whereas, the cells in pellet are compacted into a small area and therefore are just increasing in density over the period of evaluation. Arguably, there is really no room for much volume increase since they are already in a pellet.

What is claimed is:

1. A method of repairing a calvarial defect with small intestine submucosa (SIS) seeded with muscle-derived progenitor cells (MDCs) in a mammalian subject in need thereof comprising:
 (a) providing MDCs, wherein the MDCs are isolated by:
  (i) isolating skeletal muscle from a mammal,
  (ii) suspending the mammalian skeletal muscle in a medium in a first cell culture container for between 30 and 120 minutes thereby producing a cell population of adherent cells and a population of non-adherent cells;
  (iii) decanting the medium and the population of the non-adherent cells from the first cell culture container to a second cell culture container;
  (iv) allowing the population of the decanted non-adherent cells in the medium from the first cell culture container to attach to the walls of the second cell culture container for 1-3 days;
  (v) isolating the population of cells from the walls of the second cell culture container, wherein the isolated cells are MDCs;
 (b) providing SIS;
 (c) seeding the SIS with the MDCs twelve hours before transplantation to the calvarial defect of the subject; and (d) transplanting the MDC seeded SIS produced by step c to the calvarial defect of the mammalian subject;

thereby, repairing the calvarial defect in the mammalian subject in need thereof, wherein the MDCs express desmin.

2. The method of claim 1, wherein the MDC is seeded onto a single layer SIS sheet and positioned in the interior of the bone.

3. The method of claim 1, wherein the mammal is a human.

4. The method of claim 1, wherein the MDCs are cultured to expand their number before being used to seed the SIS.

5. The method of claim 1, wherein the calvarial defect is repaired by formation of new bone.

6. The method of claim 5, wherein the new bone is formed within 4 weeks.

7. The method of claim 5, wherein the new bone is formed within 10 weeks.

\* \* \* \* \*